(12) United States Patent
Ron et al.

(10) Patent No.: US 7,666,587 B2
(45) Date of Patent: Feb. 23, 2010

(54) METHOD OF SCREENING TEST SUBSTANCES FOR TREATING OR PREVENTING A DISEASE MEDIATED BY PLASMA CELLS

(75) Inventors: David Ron, New York, NY (US); Marcella Calfon, New York, NY (US); Heather Harding, Brooklyn, NY (US); Yuhong Zhang, Elmhurst, NY (US)

(73) Assignee: New York University, New York, NY (US)

( * ) Notice: Subject to any disclaimer, the term of this patent is extended or adjusted under 35 U.S.C. 154(b) by 845 days.

(21) Appl. No.: 10/413,538

(22) Filed: Apr. 11, 2003

(65) Prior Publication Data

US 2003/0224428 A1 Dec. 4, 2003

Related U.S. Application Data

(60) Provisional application No. 60/372,497, filed on Apr. 12, 2002.

(51) Int. Cl.
*C12Q 1/68* (2006.01)
(52) U.S. Cl. .............................. 435/6; 435/4
(58) Field of Classification Search ............... 435/4, 435/6, 7.1, 194.1; 436/501
See application file for complete search history.

(56) References Cited

U.S. PATENT DOCUMENTS 5,625,048 A * 4/1997 Tsien et al. ............... 536/23.4
6,632,608 B2 * 10/2003 Glimcher et al. ............ 506/10

OTHER PUBLICATIONS

Shamu, C.E. et al, The EMBO Journal, 15(12): 3028-3039, 1996.*
Wen, X.-Y., et al., International Journal of Oncology, 15: 173-178, 1999.*
Galfre, G. and C. Milstein, Methods in Enzymology, 73: 3-46, 1981.*
Bertolotti, A., et al., Nature Cell Biology, 2: 326-332, Jun. 2000.*
Chen, L. et al., The Journal of Biological Chemistry, 275(41): 32227-32233, Oct. 2000.*
Zajac-Kaye, M. et al., Biochem. J. 345: 535-541, 2000.*
Yoshida, H. et al., Cell Struct. Funct. 31(2): 117-125, 2006.*
Adams, "Proteasome Inhibition in Cancer: Development of PS-341," *Semin. Oncol.* 28:613-619 (2001).
Calame et al., "Regulatory Mechanisms That Determine the Development and Function of Plasma Cells," *Annu. Rev. Immunol.* 21:205-230 (2003).
Calfon et al., "IRE1 Couples Endoplasmic Reticulum Load to Secretory Capacity by Processing the *XBP-1* mRNA," *Nature* 415:92-96 (2002).
Calfon et al., "Corrigendum: IRE1 Couples Endoplasmic Reticulum Load to Secretory Capacity By Processing the XBP-1 mRNA," *Nature* 420:202 (2002).
Claudio et al., "A Molecular Compendium of Genes Expressed in Multiple Myeloma," *Blood* 100:2175-2186 (2002).
Felmlee et al., "Hepatitis C Virus Induces ER Stress; XBP-1 Converges Disease and Replication," in Kaufman et al., eds., *Conformational Diseases of the Secretory Pathway*, Meetings on Biomedical and Life Sciences that Encourage Scientific Information Exchange and Networking, Keystone Symposia, 2003 Abstract Book, Taos, New Mexico, Mar. 1-6, 2003 (Abstract).
Gass at al., "Activation of an Unfolded Protein Response During Differentiation of Antibody-Secreting B Cells," *J. Biol. Chem*, 277:49047-49054 (2002).
Harding at al., "Translational Regulation of Gene Expression In the Cellular Response to Biosynthetic Load on the Endoplasmic Reticulum," 4th West Coast Meeting on mRNA Stability and Translation, Seattle, WA, Oct. 14-16, 2001 (Abstract).
Holtz et al., "Parkinsonian Mimetics Induce Aspects of Unfolded Protein Response in Death of Dopaminergic Neurons," *J. Biol. Chem. Papers In Press*, published as Manuscript M211821200 (2003).
Iwakoshi et al., "Plasma Cell Differentiation and the Unfolded Protein Response Intersect at the Transcription Factor XBP-1," *Nat. Immunol.* 4(4):321-329 (2003).
Lee et al., "IRE1-Mediated Unconventional mRNA Splicing and S2P-Mediated ATF6 Cleavage Merge to Regulate XBP1 in Signaling the Unfolded Protein Response," *Genes Dev.* 16:452-466(2002).
Lee, "The Glucose-Regulated Proteins: Stress Induction and Clinical Applications," *Trends Biochem. Sci.* 26:504-510 (2001).
Reimold et al., "Plasma Cell Differentiation Requires the Transcription Factor XBP-1," *Nature* 412:300-307 (2001).
Ryu et al., "Endoplasmic Reticulum Stress and the Unfolded Protein Response in Cellular Models of Parkinson's Disease," *J. Neurosci.* 22:10690-10698 (2002).
Shen et al., "Complementary Signaling Pathways Regulate the Unfolded Protein Response and Are Required for *C. elegans* Development," *Cell* 107:893-903 (2001).
Urano et al., "A Survival Pathway for *Caenorhabditis elegans* with a Blocked Unfolded Protein Response," *J. Cell. Biol.* 158:639-646 (2002).
Yoshida et al., "A Time-Dependent Phase Shift in the Mammalian Unfolded Protein Response," *Dev. Cell.* 4:265-271 (2003).
Yoshida et al., "XBP1 mRNA Is Induced by ATF6 and Spliced by IRE1 in Response to ER Stress to Produce a Highly Active Transcription Factor," *Cell* 107:881-891 (2001).

* cited by examiner

*Primary Examiner*—Alana M. Harris
*Assistant Examiner*—Anne L Holleran
(74) *Attorney, Agent, or Firm*—Nixon Peabody LLP

(57) ABSTRACT

The present invention relates to a method of screening a compound for potential effectiveness in treating or preventing a mammalian disease mediated by plasma cells or a mammalian disease caused by virus infection of mammalian cells. Compounds are tested for their ability to inhibit IRE1-mediated processing of untranslatable XBP-1 mRNA into translatable XBP-1 mRNA. Drugs that are useful in treating or preventing a mammalian disease mediated by plasma cells and a method for detecting XBP-1 activity in living cells are also described.

7 Claims, 15 Drawing Sheets

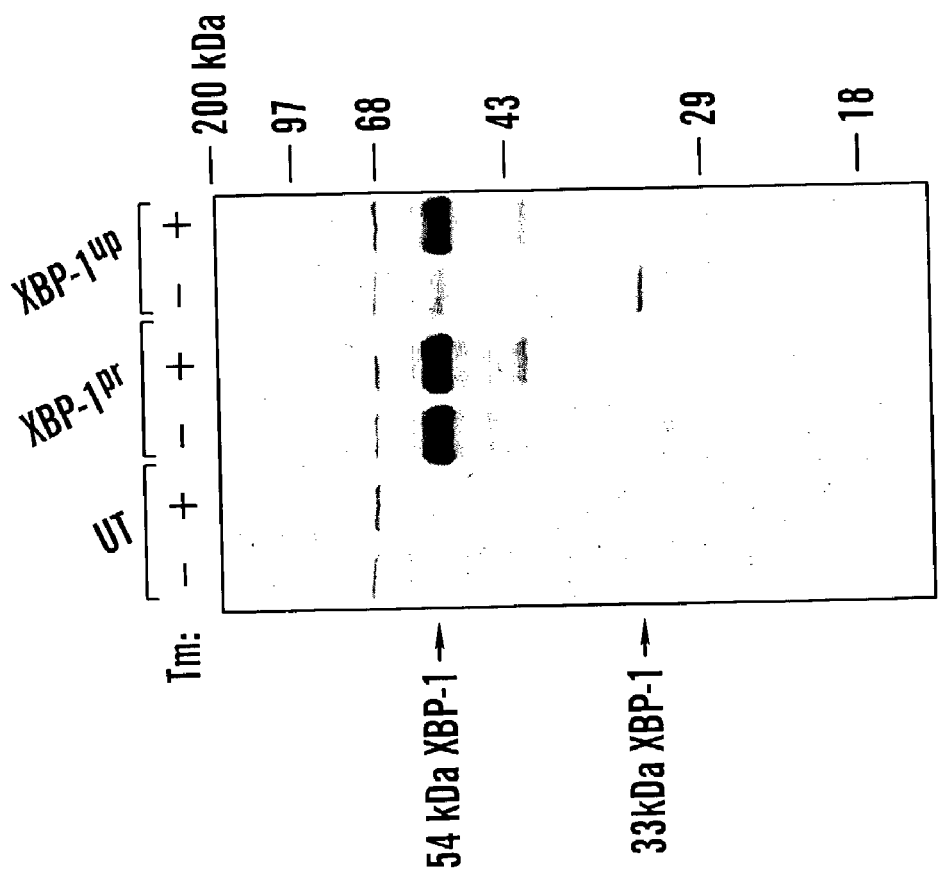

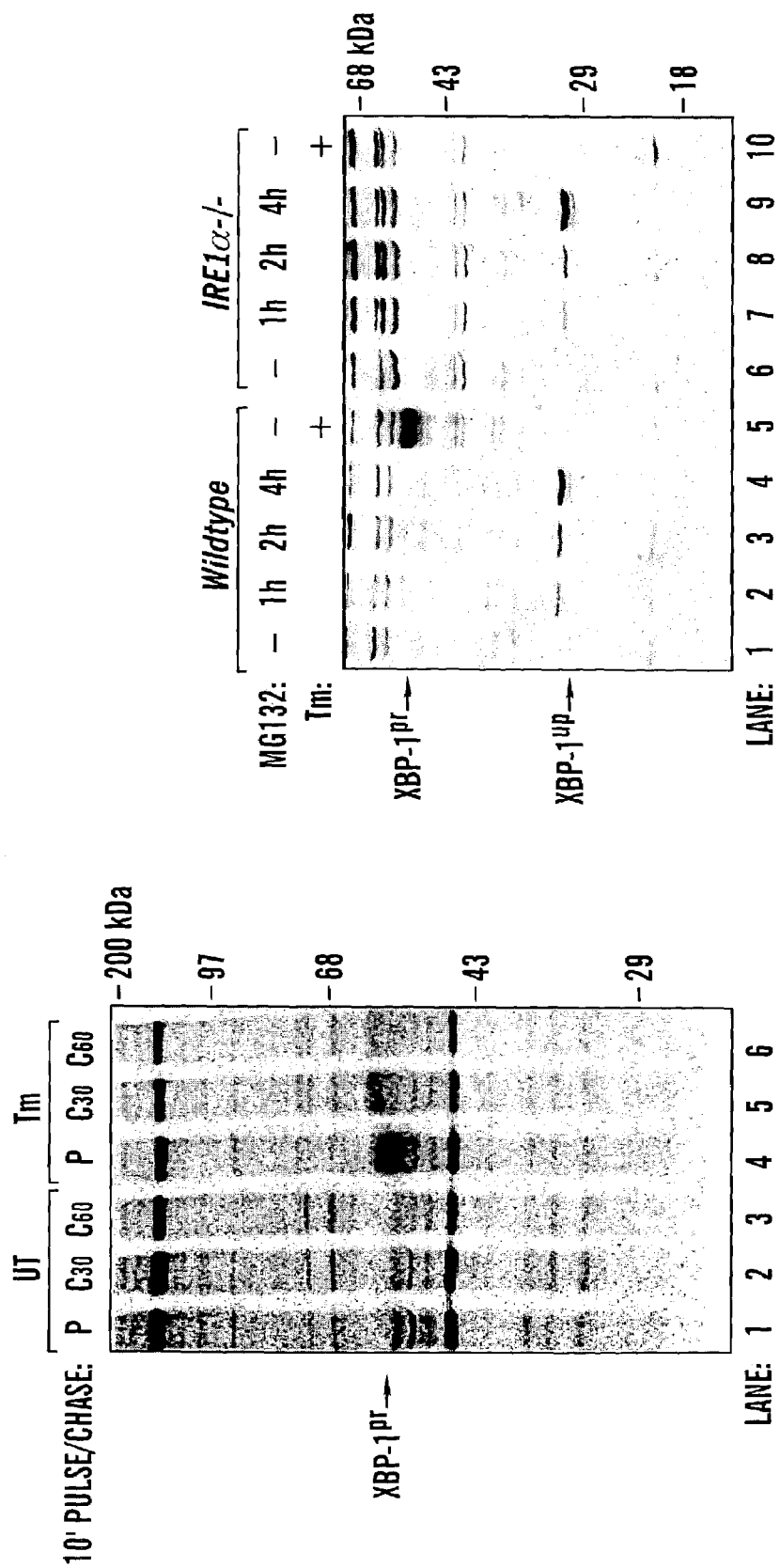

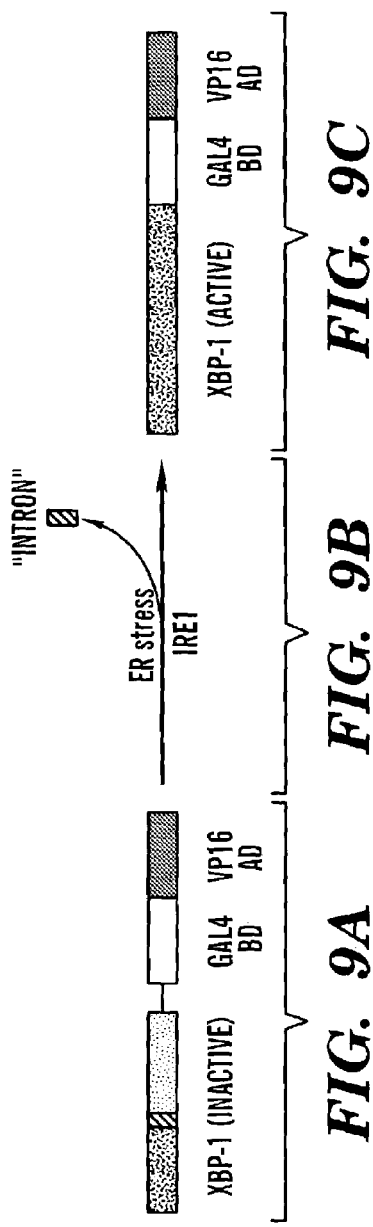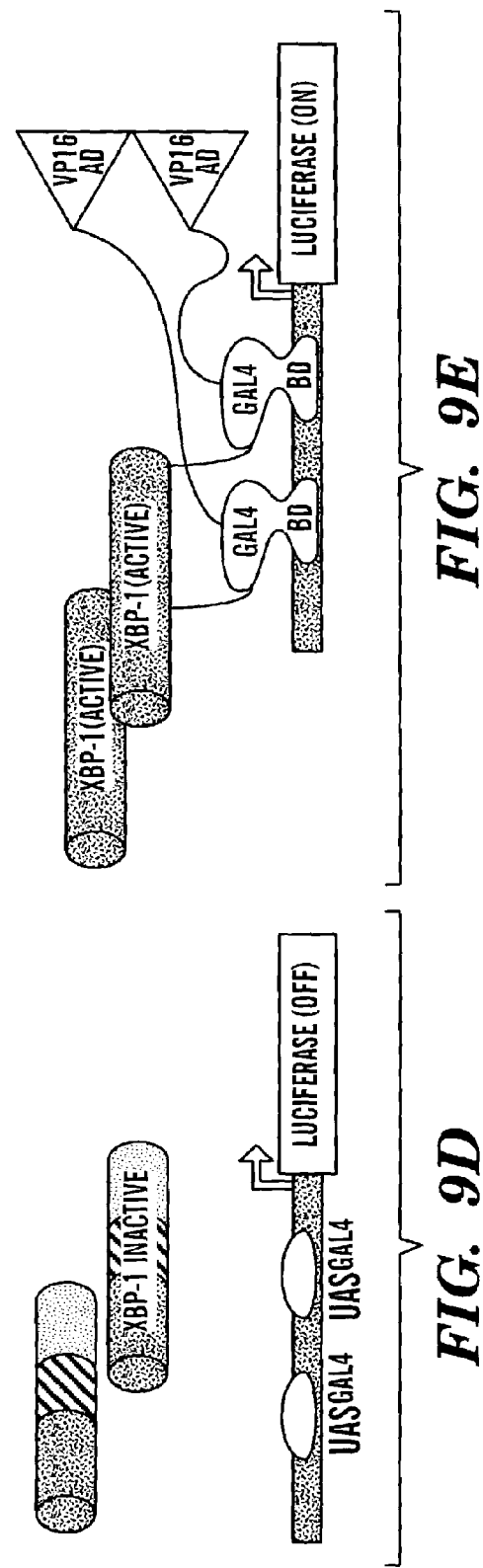
*FIG. 9A*  *FIG. 9B*  *FIG. 9C*
*FIG. 9D*  *FIG. 9E*

SEQUENCE LISTING

```
<160> NUMBER OF SEQ ID NOS: 8

<210> SEQ ID NO 1
<211> LENGTH: 57
<212> TYPE: RNA
<213> ORGANISM: Mouse

<400> SEQUENCE: 1
ucugcugagu ccgcagcacu cagacuaugu gcaccucugc agcaggugca ggcccag      57

<210> SEQ ID NO 2
<211> LENGTH: 57
<212> TYPE: RNA
<213> ORGANISM: Human

<400> SEQUENCE: 2
ucugcugagu ccgcagcacu cagacuacgu gcaccucugc agcaggugca ggcccag      57

<210> SEQ ID NO 3
<211> LENGTH: 54
<212> TYPE: RNA
<213> ORGANISM: Caenorhabditis elegans

<400> SEQUENCE: 3
gccuuugaau cagcagcauu cauuaaugag ccucagcagu gggaacaggc ccga         54

<210> SEQ ID NO 4
<211> LENGTH: 280
<212> TYPE: RNA
<213> ORGANISM: Yeast
<220> FEATURE:
<221> NAME/KEY: misc_feature
<222> LOCATION: (26)..(252)
<223> OTHER INFORMATION: n is a or g or c or u

<400> SEQUENCE: 4
uggcguaauc cagccgugau uacgannnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnguacuguc cgaagcgcag ucagguuuga                          280

<210> SEQ ID NO 5
<211> LENGTH: 25
<212> TYPE: DNA
<213> ORGANISM: Artificial
<220> FEATURE:
<223> OTHER INFORMATION: Primer
```

<400> SEQUENCE: 5
gcaccttcta gaagctacac tagca                                            25

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
aaacagagta gcagcgcaga ctgc                                             24

<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7
ggatctctaa aactagaggc ttggtg                                           26

<210> SEQ ID NO 8
<211> LENGTH: 6737
<212> TYPE: DNA
<213> ORGANISM: Artificial
<220> FEATURE:
<223> OTHER INFORMATION: Artificial gene
<220> FEATURE:
<221> NAME/KEY: misc_feature
<222> LOCATION: (3604)..(3604)
<223> OTHER INFORMATION: n is a or g or c or t
<220> FEATURE:
<221> NAME/KEY: misc_feature
<222> LOCATION: (5555)..(5556)
<223> OTHER INFORMATION: n is a or g or c or t
<220> FEATURE:
<221> NAME/KEY: misc_feature
<222> LOCATION: (5558)..(5558)
<223> OTHER INFORMATION: n is a or g or c or t
<220> FEATURE:
<221> NAME/KEY: misc_feature
<222> LOCATION: (5561)..(5561)
<223> OTHER INFORMATION: n is a or g or c or t
<220> FEATURE:
<221> NAME/KEY: misc_feature
<222> LOCATION: (5571)..(5571)
<223> OTHER INFORMATION: n is a or g or c or t
<220> FEATURE:
<221> NAME/KEY: misc_feature
<222> LOCATION: (5620)..(5620)
<223> OTHER INFORMATION: n is a or g or c or t
<220> FEATURE:
<221> NAME/KEY: misc_feature
<222> LOCATION: (5631)..(5631)
<223> OTHER INFORMATION: n is a or g or c or t

<400> SEQUENCE: 8
gacgcgccct gtagcggcgc attaagcgcg gcgggtgtgg tggttacgcg cagcgtgacc     60
gctacacttg ccagcgccct agcgcccgct cctttcgctt tcttcccttc ctttctcgcc    120
acgttcgccg gctttccccg tcaagctcta atcgggggc tccctttagg gttccgattt    180
agtgctttac ggcacctcga ccccaaaaaa cttgattagg gtgatggttc acgtagtggg    240
ccatcgccct gatagacggt ttttcgccct ttgacgttgg agtccacgtt ctttaatagt    300
ggactcttgt tccaaactgg aacaacactc aaccctatct cggtctattc ttttgattta    360

| | |
|---|---|
| taagggattt tgccgatttc ggcctattgg ttaaaaaatg agctgattta acaaaaattt | 420 |
| aacgcgaatt ttaacaaaat attaacgttt acaatttcag gtggcacttt tcggggaaat | 480 |
| gtgcgcggaa ccoctatttg tttatttttc taaatacatt caaatatgta tccgctcatg | 540 |
| ccaggtcttg gactggtgag aacggcttgc tcggcagctt cgatgtgtgc tggagggaga | 600 |
| ataaaggtct aagatgtgcg atagagggaa gtcgcattga attatgtgct gtgtagggat | 660 |
| cgctggtatc aaatatgtgt gcccacccct ggcatgagac aataaccctg ataaatgctt | 720 |
| caataatatt gaaaaaggaa gagtatgagt attcaacatt tccgtgtcgc ccttattccc | 780 |
| tttttttgcgg catttttgcct tcctgttttt gctcacccag aaacgctggt gaaagtaaaa | 840 |
| gatgctgaag atcagttggg tgcacgagtg ggttacatcg aactggatct caacagcggt | 900 |
| aagatccttg agagttttcg ccccgaagaa cgttttccaa tgatgagcac ttttaaagtt | 960 |
| ctgctatgtg gcgcggtatt atcccgtatt gacgccgggc aagagcaact cggtcgccgc | 1020 |
| atacactatt ctcagaatga cttggttgag tactcaccag tcacagaaaa gcatcttacg | 1080 |
| gatggcatga cagtaagaga attatgcagt gctgccataa ccatgagtga taacactgcg | 1140 |
| gccaacttac ttctgacaac gatcggagga ccgaaggagc taaccgcttt tttgcacaac | 1200 |
| atggggatc atgtaactcg ccttgatcgt tgggaaccgg agctgaatga agccatacca | 1260 |
| aacgacgagc gtgacaccac gatgcctgta gcaatggcaa caacgttgcg caaactatta | 1320 |
| actggcgaac tacttactct agcttcccgg caacaattaa tagactggat ggaggcggat | 1380 |
| aaagttgcag gaccacttct gcgctcggcc cttccggctg gctggtttat tgctgataaa | 1440 |
| tctggagccg gtgagcgtgg gtctcgcggt atcattgcag cactggggcc agatggtaag | 1500 |
| ccctcccgta tcgtagttat ctacacgacg gggagtcagg caactatgga tgaacgaaat | 1560 |
| agacagatcg ctgagatagg tgcctcactg attaagcatt ggtaactgtc agaccaagtt | 1620 |
| tactcatata tactttagat tgatttaaaa cttcatttt aatttaaaag gatctaggtg | 1680 |
| aagatccttt ttgataatct catgccataa cttcgtataa tgtatgctat acgaagttat | 1740 |
| ggcatgacca aaatccctta acgtgagttt cgttccact gagcgtcaga ccccgtagaa | 1800 |
| aagatcaaag gatcttcttg agatcctttt tttctgcgcg taatctgctg cttgcaaaca | 1860 |
| aaaaaaccac cgctaccagc ggtggtttgt ttgccggatc aagagctacc aactcttttt | 1920 |
| ccgaaggtaa ctggcttcag cagagcgcag ataccaaata ctgtccttct agtgtagccg | 1980 |
| tagttaggcc accacttcaa gaactctgta gcaccgccta catacctcgc tctgctaatc | 2040 |
| ctgttaccag tggctgctgc cagtggcgat aagtcgtgtc ttaccgggtt ggactcaaga | 2100 |
| cgatagttac cggataaggc gcagcggtcg ggctgaacgg ggggttcgtg cacacagccc | 2160 |
| agcttggagc gaacgaccta caccgaactg agatacctac agcgtgagca ttgagaaagc | 2220 |
| gccacgcttc ccgaagggag aaaggcggac aggtatccgg taagcggcag gtcggaaca | 2280 |
| ggagagcgca cgagggagct tccaggggga acgcctggt atctttatag tcctgtcggg | 2340 |
| tttcgccacc tctgacttga gcgtcgattt ttgtgatgct cgtcaggggg gcggagccta | 2400 |
| tggaaaaacg ccagcaacgc ggccttttta cggttcctgg ccttttgctg gccttttgct | 2460 |
| cacatgttct ttcctgcgtt atcccctgat tctgtggata accgtattac cgcctttgag | 2520 |
| tgagctgata ccgctcgccg cagccgaacg accgagcgca gcgagtcagt gagcgaggaa | 2580 |
| gcggaagagc gcccaatacg caaaccgcct ctccccgcgc gttggccgat tcattaatgc | 2640 |
| agagcttgca attcgcgcgt ttttcaatat tattgaagca tttatcaggg ttattgtctc | 2700 |
| atgagcggat acatatttga atgtatttag aaaaataaac aaataggggt tccgcgcaca | 2760 |

```
tttccccgaa aagtgccacc tgacgtctaa gaaaccatta ttatcatgac attaacctat    2820
aaaaataggc gtagtacgag gcccttcac tcattagatg catgtcgtta cataacttac    2880
ggtaaatggc ccgcctggct gaccgcccaa cgaccccgc ccattgacgt caataatgac    2940
gtatgttccc atagtaacgc caatagggac tttccattga cgtcaatggg tggagtattt    3000
acggtaaact gcccacttgg cagtacatca agtgtatcat atgccaagta cgccccctat    3060
tgacgtcaat gacggtaaat ggcccgcctg gcattatgcc cagtacatga ccttatggga    3120
ctttcctact tggcagtaca tctacgtatt agtcatcgct attaccatgg tgatgcggtt    3180
ttggcagtac atcaatgggc gtggatagcg gtttgactca cggggatttc caagtctcca    3240
ccccattgac gtcaatggga gtttgttttg gcaccaaaat caacgggact ttccaaaatg    3300
tcgtaacaac tccgccccat tgacgcaaat gggcggtagg cgtgtacggt gggaggtcta    3360
tataagcaga gctcgtttag tgaaccgtca gatcgcctgg agacgccatc cacgctgttt    3420
tgacctccat agaagacacc gggaccgatc cagcctccgg actctagcct aggccgcgga    3480
gcggataaca atttcacaca ggaaacagct atgaccatta ggcctattta ggtgacacta    3540
tagaacaagt ttgtacaaaa aagcaggctg gtaccggtcc ggaattcccg ggatatcgtc    3600
gacngtagac gtttcctggc tatggtggtg gtggcagcgg cgccgagcgc ggccacggcg    3660
gcccccaaag tgctactctt atctggccag cccgcctccg gcggccgggc gctgccgctc    3720
atggtacccg gtccgcgggc agcagggtcg gaggcgagcg ggacacgcag gctcgcaagc    3780
ggcagcctca cgcacctgag cccggaggag aaagcgctgc ggaggaaact gaaaaacaga    3840
gtagcagcgc agactgctcg agatagaaag aaagcccgga tgagcgagct ggagcagcaa    3900
gtggtggatt tggaagaaga gaaccacaaa ctccagctag aaaatcagct tttacgggag    3960
aaaactcacg gccttgtggt tgagaaccag gagttaagaa cacgcttggg aatggacacg    4020
ctggatcctg acgaggttcc agaggtggag gccaagggga gtggagtaag gctggtggcc    4080
gggtctgctg agtccgcagc actcagacta tgtgcacctc tgcagcaggt gcaggcccag    4140
ttgtcacctc cccagaacat cttcccatgg actctgacac tgttgcctct tcagattctg    4200
agtctgatat ccttttgggc attctggaca agttggaccc tgtcatgttt ttcaaatgtc    4260
cttccccaga gtctgctagt ctggaggaac tcccagaggt ctacccagaa ggacctagtt    4320
ccttaccagc ctcccttttct ctgtcagtgg ggacctcatc agccaagctg gaagccatta    4380
atgaactcat tcgttttgac catgtataca ccaagcctct agttttagag atccctctg     4440 agacagagag tcaaactaac gtggtagtga aaattgagga agcacctcta agctcttcag    4500
aagaggatca ccctgaattc attgtctcag tgaagaaaga gcctttggaa gatgacttca    4560
tcccagagct gggcatctca aacctgcttt catccagcca ttgtctgaga ccaccttctt    4620
gcctgctgga cgctcacagt gactgtggat atgagggctc cccttctccc ttcagtgaca    4680
tgtcttctcc acttggtaca gaccactcct gggaggatac ttttgccaat gaacttttcc    4740
cccagctagc gctactgtct tctatcgaac aagcatgcga tatttgccga cttaaaaagc    4800
tcaagtgctc caaagaaaaa ccgaagtgcg ccaagtgtct gaagaacaac tgggagtgtc    4860
gctactctcc caaaaccaaa aggtctccgc tgactagggc acatctgaca gaagtggaat    4920
caaggctaga aagactggaa cagctatttc tactgatttt tcctcgagaa gaccttgaca    4980 tgatttgaa aatggattct ttacaggata taaaagcatt gttaacagga ttatttgtac    5040
aagataatgt gaataaagat gccgtcacag atagattggc ttcagtggag actgatatgc    5100
```

```
ctctaacatt gagacagcat agaataagtg cgacatcatc atcggaagag agtagtaaca    5160
aaggtcaaag acagttgact gtatcgccgg aattcccggg gatctgggcc cccccgaccg    5220
atgtcagcct gggggacgag ctccacttag acggcgagga cgtggcgatg gcgcatgccg    5280
acgcgctaga cgatttcgat ctggacatgt tgggggacgg ggattccccg ggtccgggat    5340
ttacccccca cgactccgcc ccctacggcg ctctggatat ggccgacttc gagtttgagc    5400
agatgtttac cgatgccctt ggaattgacg agtacggtgg gtagggggcg cgaccggacc    5460
cgcatccccc ccgtctgggt tttcccctcc cgtccccgg tttcgtatcc acataaacac    5520
gagcacatac attacaaaaa cctgcggttg tcgtnnanat ntcgaaggtt natgaaacac    5580
ggaagcagac aataccggaa ggaacccgcg cctatgacgn caataaaaag ncagaataaa    5640
acgcacgggt gttgggtcgt ttgttcataa acgcggggtt cggtcccagg gctggcactc    5700
tgtcgatacc ccaccgagac cccattgggg ccaatacgcc cgcgtttctt ccttttcccc    5760
accccacccc ccaagttcgg gtgaaggcc agggctcgca gccaacgtcg gggcggcagg    5820
ccctgccata gccactggcc ccgtgggtta gggacggggt cccccatggg gaatggttta    5880
tggttcgtgg gggttattat tttgggcgtt gcgtggggtc aggtccacga cccaagcttg    5940
tcgacggtac cccgggggaat tcgagctcta gagtatccct cgaggggccc aagcttacgc    6000
gtacccagct ttcttgtaca aagtggtccc tatagtgagt cgtattataa gctaggcact    6060
ggccgtcgtt ttacaacgtc gtgactggga aaactgctag cttgggatct ttgtgaagga    6120
accttacttc tgtggtgtga cataattgga caaactacct acagagattt aaagctctaa    6180
ggtaaatata aaattttaa gtgtataatg tgttaaacta gctgcatatg cttgctgctt    6240
gagagttttg cttactgagt atgatttatg aaaatattat acacaggagc tagtgattct    6300
aattgtttgt gtatttaga ttcacagtcc caaggctcat ttcaggcccc tcagtcctca    6360
cagtctgttc atgatcataa tcagccatac cacatttgta gaggttttac ttgctttaaa    6420
aaacctccca cacctccccc tgaacctgaa acataaaatg aatgcaattg ttgttgttaa    6480
cttgtttatt gcagcttata atggttacaa ataaagcaat agcatcacaa atttcacaaa    6540
taaagcattt ttttcactgc attctagttg tggtttgtcc aaaactcatca atgtatctta    6600 tcatgtctgg atcgatcctg cattaatgaa tcggccaacg cgcggggaga ggcggtttgc    6660
gtattggctg gcgtaatagc gaagaggccc gcaccgatcg cccttcccaa cagttgcgca    6720
gcctgaatgg cgaatgg                                                   6737
```

METHOD OF SCREENING TEST SUBSTANCES FOR TREATING OR PREVENTING A DISEASE MEDIATED BY PLASMA CELLS

This application claims the benefit of U.S. Provisional Patent Application Ser. No. 60/372,497, filed Apr. 12, 2002.

The subject matter of this application was made with support from the United States Government under PHS Award 2R01 DK47119 and PHS Award 2R01 ES08681. The United States Government may have certain rights.

FIELD OF THE INVENTION

The present invention relates to methods of screening test substances for treating or preventing a disease mediated by plasma cells or caused by viruses, as well as drugs suitable for treating or preventing these diseases.

BACKGROUND OF THE INVENTION

Plasma cells are the major immunoglobulin-producing cells in humans. While a great deal has been learned in recent years on the development of the B cell lymphoid lineage that gives rise to plasma cells, there has been very little molecular insight into the process of plasma cell development and maintenance. For this reason there are at present few, if any, useful pharmacological tools for manipulating plasma cell development and function. It is highly likely that drugs that would interfere with plasma cell development and function would be useful in treating human diseases caused by pathogenic immunoglobulins (that are produced by plasma cells). Such drugs would also be useful in treating diseases such as Multiple Myeloma, a common human cancer in which plasma cells proliferate abnormally.

XBP-1 (X-box binder protein 1), which encodes a transcription factor, has been described as playing a role in plasma cell development, as reported by Reimold et al., "Plasma Cell Differentiation Requires the Transcription Factor XBP-1," Nature 412:300-307 (2001). In that study, mice lacking the XBP-1 gene were unable to develop plasma cells and had impaired immunoglobulin secretion. Because of the apparent crucial role of XBP-1 in plasma cell development and function, Reimold et al. suggested that a drug that would prevent XBP-1 action or expression would be useful. However, because it is very difficult to inhibit a transcription factor (such as XBP-1), it is not likely that XBP-1 would be a good drug target for developing treatments of diseases associated with plasma cell function. Thus, rather than directly targeting XBP-1 as a means for inhibiting plasma cell development, targeting other factors in the XBP-1 pathway may be useful in developing drugs or other treatments for diseases associated with plasma cell development.

IRE1 is a stress-activated endonuclease that resides in the endoplasmic reticulum. The processing of XBP-1 by IRE1 has been previously reported (Shen et al., "Complementary Signaling Pathways Regulate the Unfolded Protein Response and are Required for C. elegans Development," Cell 107:893-903 (2001), Yoshida et al., "XBP1 mRNA is Induced by ATF6 and Spliced by IRE1 in Response to ER Stress to Produce a Highly Active Transcription Factor," Cell 107:881-891 (2001), and Calfon et al., "IRE1 Couples Endoplasmic Reticulum Load to Secretory Capacity by Processing the XBP-1 mRNA," Nature 415:92-96 (2002)). However, knowledge in the art of how to develop treatments for plasma cell associated diseases by targeting the XBP-1 pathway, and particularly IRE1, is not well developed. In particular, it would be important to the medical community to have assays that screen for compounds that can be developed into drugs for inhibiting plasma cell development and function. Currently, the only drugs known to inhibit abnormal plasma cells are proteasome inhibitors that are in clinical trials (Adams, "Proteasome Inhibition in Cancer: Development of PS-341," Semin. Oncol. 28: 613-9 (2001)).

The present invention is directed to overcoming these and other deficiencies in the art.

SUMMARY OF THE INVENTION

The present inventions relates to a method of screening a compound for potential effectiveness in treating or preventing a mammalian disease mediated by plasma cells. This method involves providing a test compound. The test compound is subjected to an assay system suitable for evaluating the test compound's ability to inhibit processing of untranslatable XBP-1 mRNA to translatable XBP-1 mRNA. The method further involves identifying test compounds that inhibit processing of untranslatable XBP-1 mRNA to translatable XBP-1 mRNA as having potential effectiveness in treating or preventing a mammalian disease mediated by plasma cells.

The present invention also relates to a method of screening a compound for potential effectiveness in treating or preventing a mammalian disease caused by virus infection of mammalian cells. This method involves providing a test compound. The test compound is subjected to an assay system suitable for evaluating the test compound's ability to inhibit processing of untranslatable XBP-1 mRNA to translatable XBP-1 mRNA. The method further involves identifying test compounds that inhibit processing of untranslatable XBP-1 mRNA to translatable XBP-1 mRNA as having potential effectiveness in treating or preventing a mammalian disease caused by virus infection of mammalian cells.

The present invention also relates to a drug useful in treating or preventing a mammalian disease caused by plasma cells. In one embodiment, the drug may include a therapeutic compound that inhibits the processing of untranslatable XBP-1 mRNA to translatable XBP-1 mRNA.

The present invention also relates to a method of detecting the activity of XBP-1 in living cells. This method involves providing a living cell transfected with an artificial XBP-1/reporter gene. A suitable artificial XBP-1/reporter gene may include a coding region for untranslatable XBP-1 and a reporter gene. The living cell is provided under conditions effective to allow the reporter gene to express a reporter protein or polypeptide product only when untranslatable XBP-1 is processed into translatable XBP-1. In this method, the living cell is contacted with an endoplasmic reticulum stress-inducing agent under conditions effective to activate processing of untranslatable XBP-1 mRNA to translatable mRNA. The method further involves detecting the presence of the protein or polypeptide product of the reporter gene in the living cells using an assay system. The presence of the protein or polypeptide product indicates activity of XBP-1 in the living cells.

BRIEF DESCRIPTION OF THE DRAWINGS

FIGS. 3A-3I are fluorescent photomicrographs of various treatments used to identify mutants in the *C. elegans* UPR. FIG. 3A shows results of an untreated adult hsp-4::gfp(zcIs4)V transgenic animal. The white arrowheads track the outline of the body. The arrows indicate the spermatheca. FIG. 3B shows results of an hsp-4::gfp(zcIs4)V animal treated with the ER-stress causing drug tunicamycin. FIG. 3C shows results of a tunicamycin-treated ire-1(RNAi)II; hsp-4::gfp(zcIs4) V animal. FIG. 3D shows results of an untreated hsp-4::gfp(zcIs4)V, (zc6)X animal (note constitutive activation of the UPR in the posterior gut). FIG. 3E shows results of an untreated hsp-4:: gfp(zcIs4)V; upr-1(zc6)X animal with a second mutation in ire-1(zc14)II. FIG. 3F shows results of a tunicamycin-treated ire-1(zc14)II; hsp-4::gfp(zcIs4)V animal. FIG. 3G shows results of an untreated hsp-4::gfp(zcIs4)V; upr-1(zc6)X animal with a second mutation in xbp-1(zc12)III. FIG. 3H shows results of a tunicamycin-treated xbp-1(zc12)III; hsp-4::gfp (zcIs4) V animal. FIG. 3I shows results of a tunicamycin-treated xbp-1(RNAi)III; hsp-4::gfp(zcIs4)V animal. FIG. 3J shows results of a northern blot of hsp-4 RNA from untreated and tunicamycin treated (Tm) wildtype (WT), ire-1(zc10)II or xbp-1(zc12)III mutant animals. Integrity and loading of the RNA is revealed by ethidium bromide staining of the ribosomal bands.

FIG. 4A is an XBP-1 immunoblot from murine fibroblasts treated with tunicamycin (Tm, upper panel) or thapsigargin (Tg, middle panel). CHOP immunoblot of the thapsigargin-treated lysates provides a positive control for the induction of the UPR (lower panel). FIG. 4B is an XBP-1 immunoblot of lysates of differentiating mouse spleen cells cultured in media with or without bacterial lipopolysaccharide (LPS) for the indicated number of days and lysates of untreated and tunicamycin-treated fibroblasts. CREB (lower panel) serves as a loading and recovery control. FIG. 4C shows XBP-1, CHOP, and CREB immunoblots and XBP-1 and β-Actin Northern blots from untreated and tunicamycin treated cells with the indicated genotypes.

FIG. 5A show autoradiograms of a Southern blot of undigested or Pst1-digested XBP-1 cDNA, from untreated (UT), tunicamycin (Tm), thapsigargin (Tg), dithiothreitol (DTT) or sodium arsenite (As) treated wildtype or IRE1 mutant cells. The unprocessed (UP) and processed (PR) cDNA fragments are indicated by the arrows to the left of the autoradiograms. FIG. 5B is a map of the unprocessed and processed murine XBP-1 mRNAs. The coding regions are boxed, the bZIP domain is indicated, and the intron excised by IRE1 is darkly shaded and appears to the right of the bZIP domain. The open reading frame in the processed mRNA is hatched. FIG. 5C shows the alignment of the RNA sequence surrounding and including the intron in the mouse (SEQ ID NO:1), human (SEQ ID NO:2), and *C. elegans* XBP-1 (SEQ ID NO:3) and yeast HAC1 (SEQ ID NO:4). The predicted stem-loop structures cleaved by IRE1 are represented by opposing arrows (stems) flanking the semicircle (loop). Conserved residues in the loops are indicated by the consensus sequence. FIG. 5D is a schematic showing the predicted secondary structure of the mouse XBP-1 mRNA in the region surrounding the IRE1 cleavage sites (arrows). FIG. 5E is an autoradiogram of radiolabeled fragments produced by site-specific cleavage of the unprocessed (UP) or processed (PR) XBP-1 mRNA by purified IRE1 in vitro.

FIGS. 7A-7D depicts the processing of XBP-1 mRNA controls expression of the encoded protein. FIG. 7A is an immunoblot of N-terminal FLAG epitope-tagged XBP-1 from untreated or tunicamycin-treated (Tm) untransfected (UT) and cells transfected with expression plasmids containing the processed (XBP-1$^{Pr}$), or unprocessed XBP-1 cDNA (XBP-1$^{up}$). FIG. 7B is a Northern blot of mouse XBP-1 mRNA from the transfected cells. FIG. 7C is an autoradiogram of a pulse chase experiment of metabolically labeled FLAG-tagged XBP-1 proteins from transfected cells and the corresponding logarithmic plot of the radioactive signal as a function of time. FIG. 7D is an autoradiogram of metabolically labeled endogenous XBP-1 proteins from untreated, tunicamycin (Tm) and proteasome inhibited (PI) wildtype and IRE1 mutant mouse fibroblasts.

FIGS. 8A-8B show the measuring of the half-life of endogenous XBP-1$^{Pr}$ and detecting endogenous XBP-1$^{up}$ by immunoblot. FIG. 8A is an autoradiogram of a pulse-chase experiment of metabolically-labeled endogenous XBP-1 proteins from untreated (UT) and tunicamycin-treated (Tm) wildtype cells. FIG. 8B is an immunoblot of endogenous XBP-1 proteins in wildtype and IRE1 mutant mouse fibroblasts treated with the proteasomal inhibitor, MG132 or tunicamycin (Tm).

FIGS. 9A-9E are schematic drawings showing a sensitive reporter system for measuring XBP-1 activation in living cells. GAL4-VP16 is an artificial gene encoding the DNA binding domain (BD) of yeast GAL4 fused to the transcription activation domain (AD) of Herpes Simplex Virus VP16 gene. The encoded fusion protein, GAL4-VP16, will bind to special GAL4 UAS sites. Such sites are normally absent in mammalian genes, but can be introduced into a luciferase reporter gene. This UAS-Luciferase reporter is therefore subordinate to activation by GAL4-VP16, which is normally absent from mammalian cells. Fusion of the coding region of GAL4-VP16 to XBP-1 will render it translatable only upon processing of the XBP-1 mRNA by IRE1. Thus, Luciferase activity in cells carrying this system is indicative of activity of the entire IRE1 and XBP-1 pathway.

DETAILED DESCRIPTION OF THE INVENTION

The present inventions relates to a method of screening a compound for potential effectiveness in treating or preventing a mammalian disease mediated by plasma cells. This method involves providing a test compound. The test compound is subjected to an assay system suitable for evaluating the test compound's ability to inhibit processing of untranslatable XBP-1 mRNA to translatable XBP-1 mRNA. The method further involves identifying test compounds that inhibit processing of untranslatable XBP-1 mRNA to translatable XBP-1 mRNA as having potential effectiveness in treating or preventing a mammalian disease mediated by plasma cells.

The various embodiments of the methods of the present invention are designed to take advantage of the knowledge that XBP-1 is activated by IRE1. Identifying compounds that block or disrupt XBP-1 activation is a crucial step in developing drugs or other treatments to prevent or treat various plasma cell mediated diseases in humans. As described more fully below, activation of XBP-1 mRNA by IRE1 entails the splicing of the XBP-1 mRNA (e.g., at nucleotide 833 of the mouse XBP-1 mRNA or the corresponding nucleotide 503 of the human XBP-1 mRNA).

Figure 1:
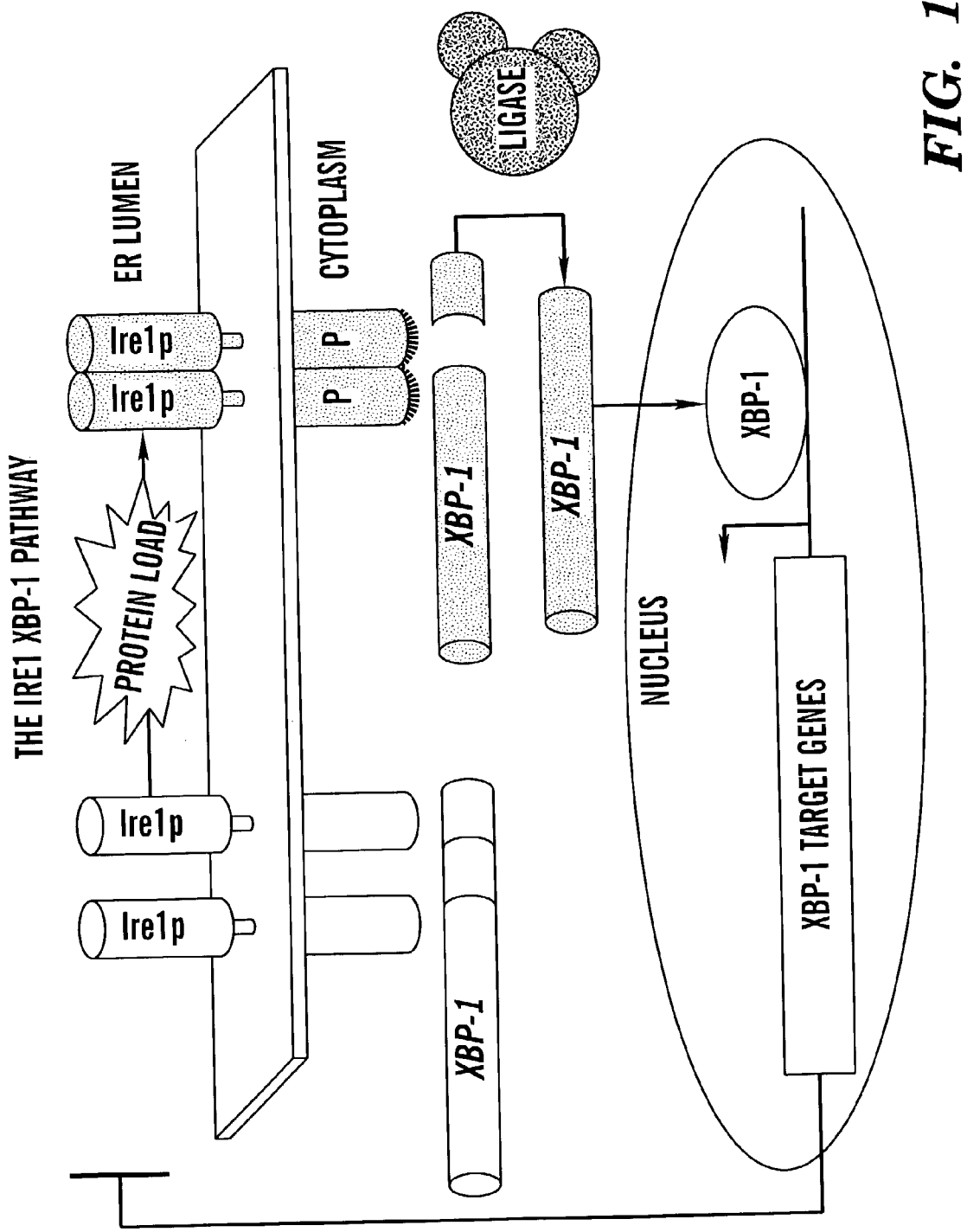
FIG. 1 is a schematic showing the events leading to XBP-1 activation in cells. IRE1 traverses the endoplasmic reticulum (ER) membrane. Its lumenal portion recognizes the load of protein in the lumen of the ER. When the protein load reaches a certain threshold (as in the developing plasma cell), IRE1 molecules associate and phosphorylate (denoted with an uppercase "P") each other. This activates IRE1 (denoted as a shaded Ire1p) and unmasks the ability of IRE1 to cleave the XBP-1 mRNA. When IRE1 is in the inactive state (denoted as a white Ire1p), the XBP-1 mRNA remains uncleaved. Active, phosphorylated (shaded) IRE1 cleaves the XBP-1 mRNA and then the two ends of the XBP-1 mRNA are ligated together to encode the active form of the XBP-1 protein, which is a nuclear transcription factor that activates its target genes. These target genes feedback on the ER to help it deal better with the load of proteins. Depriving the cell of these XBP-1 target genes by inactivating any component of the pathway described here would degrade its ability to secrete proteins to function and to survive. Drugs that inhibit the processes depicted here would be useful to treat a disease caused by plasma cells that secrete pathogenic immunoglobulins.

The IRE1/XBP-1 signal transduction pathway is illustrated in FIG. 1, and described below. Plasma cell development imposes a load of client proteins on the endoplasmic reticulum (ER) of the developing cell. This load is recognized by the lumenal domain of IRE1 and causes the self-association of two or more IRE1 protein molecules on the endoplasmic reticulum membrane. This self-association causes one IRE1 molecule to phosphorylate an adjacent IRE1 molecule. The phosphorylation of IRE1 enables it to cleave the unprocessed (also commonly referred to in the art as "unspliced") XBP-1 mRNA at the precise locations described by the inventors in Calfon et al., "IRE1 Couples Endoplasmic Reticulum Load to Secretory Capacity by Processing the XBP-1 mRNA," *Nature* 415:92-96 (2002), which is hereby incorporated by reference in its entirety. The two ends of the processed (spliced) XBP-1 mRNA are then ligated together by a cellular ligase. The ligated, processed XBP-1 mRNA is then translated into the activated XBP-1 protein that supports plasma cell development, viability, and function (FIG. 1). Disruption of this process at any level will have the consequence of impeding plasma cell function. Compounds that can achieve this goal can be developed into drugs that may be useful in treating or preventing a disease caused by or associated with plasma cells.

Thus, the present invention relates to all of the methods used to identify such compounds by applying assays whose development is based on knowledge of the IRE1-mediated processing event of the XBP-1 mRNA. For example, the present invention relates to all the methods used to determine that IRE1-mediated processing of XBP-1 mRNA has taken place and all the methods used to determine if IRE1-mediated processing of XBP-1 mRNA can or cannot take place. These methods can then be applied by one of ordinary skill in the art to high-throughput screening for compounds able to block the activation of XBP-1 in cells or in purified biochemical preparations. One suitable approach for such high throughput screens is to subject cells to a stimulus that normally activates XBP-1. A test compound, or a series of different test compounds, can then be provided to the cell in high-throughput fashion in accordance with procedures well known in the art, and the activation or inactivation of XBP-1 activity monitored for each of the test compounds.

In one aspect of the present invention, the assay system evaluates the test compound's ability to inhibit IRE1-mediated processing of untranslatable XBP-1 mRNA to translatable XBP-1 mRNA. As used herein to describe the state of the XBP-1 mRNA, the term "untranslatable" is synonymous with the terms "unspliced" and "unprocessed," and the term "translatable" is synonymous with the terms "spliced" and "processed." A suitable assay system for use in the invention includes, but is not limited to, an assay system that includes untranslatable XBP-1 mRNA, IRE1 protein, and a system suitable for translating translatable XBP-1 mRNA. A suitable means of subjecting the test compound to the assay system involves providing a stimulus effective to activate processing of untranslatable XBP-1 mRNA to translatable XBP-1 mRNA with IRE1 present. A suitable means for identifying test compounds that inhibit processing of untranslatable XBP-1 mRNA is to determine whether the test compound is effective in inhibiting the processing of untranslatable XBP-1 mRNA to translatable XBP-1 mRNA by IRE1. As used herein, the term "XBP-1 mRNA processing" refers to the process whereby untranslatable XBP-1 mRNA is processed into translatable XBP-1 mRNA.

In one embodiment, determining the effectiveness of the test compound to inhibit XBP-1 mRNA processing involves detecting whether untranslatable XBP-1 mRNA and translatable XBP-1 mRNA are present in the assay system with and without the test compound, where test compounds which reduce untranslatable XBP-1 mRNA or increase translatable XBP-1 mRNA have potential effectiveness in treating or preventing a mammalian disease mediated by plasma cells. In one aspect, detecting the amount of translatable XBP-1 mRNA and untranslatable XBP-1 mRNA present or absence in the assay system after providing the XBP-1 stimulus involves the use of a polymerase chain reaction ("PCR") process to analyze whether untranslatable XBP-1 mRNA and translatable XBP-1 mRNA are present.

One method of using PCR in the present invention is described by the inventors in Calfon et al., "IRE1 Couples Endoplasmic Reticulum Load to Secretory Capacity by Processing the XBP-1 mRNA," *Nature* 415:92-96 (2002), which is hereby incorporated by reference in its entirety. However, any other assay that might be designed based on knowledge of sites at which XBP-1 mRNA is processed by IRE1 are also contemplated by the the invention. Prior to the inventors' discovery of IRE1-mediated processing of XBP-1, it was not possible to design any such PCR-based assay, because there was no way to know where to place the primers for the reaction, or even a way to surmise that processing of XBP-1 takes place or that it represents a means for activating XBP-1 function.

In another embodiment, determining the effectiveness of the test compound to inhibit XBP-1 mRNA processing involves detecting whether a protein or polypeptide encoded by the translatable XBP-1 mRNA is present. In this embodiment, test compounds which inhibit the production of said protein or polypeptide have potential effectiveness in treating or preventing a mammalian disease mediated by plasma cells. In one aspect, the detecting involves contacting the assay system with antibodies specific to the C-terminus of the protein or polypeptide encoded by translatable XBP-1 mRNA and analyzing whether there has been any binding between the antibodies and the protein or polypeptide. Such assays can be designed based on the knowledge that the IRE1-mediated processing of XBP-1 mRNA causes a frame shift in the protein-coding region of the XBP-1 mRNA. The protein encoded by the processed XBP-1 mRNA (i.e., the activated XBP-1 protein) has unique sequences that are not present in the unprocessed mRNA (see FIG. 2). Thus, antisera reactive with this unique C-terminal extension of XBP-1 protein (FIG. 2) would detect the protein in cells able to process the mRNA but not in cells that are exposed to a compound able to block or disrupt the activation of XBP-1. The present invention contemplates the use of any assay that relies on an antisera or monoclonal antibody to detect this unique C-terminus, by any method (including, for example, immunoblot, ELISA, or immunochemistry).

Suitable antibodies include, without limitation, monoclonal or polyclonal antibodies.

Monoclonal antibody production may be effected by techniques which are well-known in the art. In general, the process involves first obtaining immune cells (lymphocytes) from the spleen of a mammal (e.g., mouse) which has been previously immunized with the antigen of interest (i.e., the protein or peptide of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference in its entirety.

Figure 2:
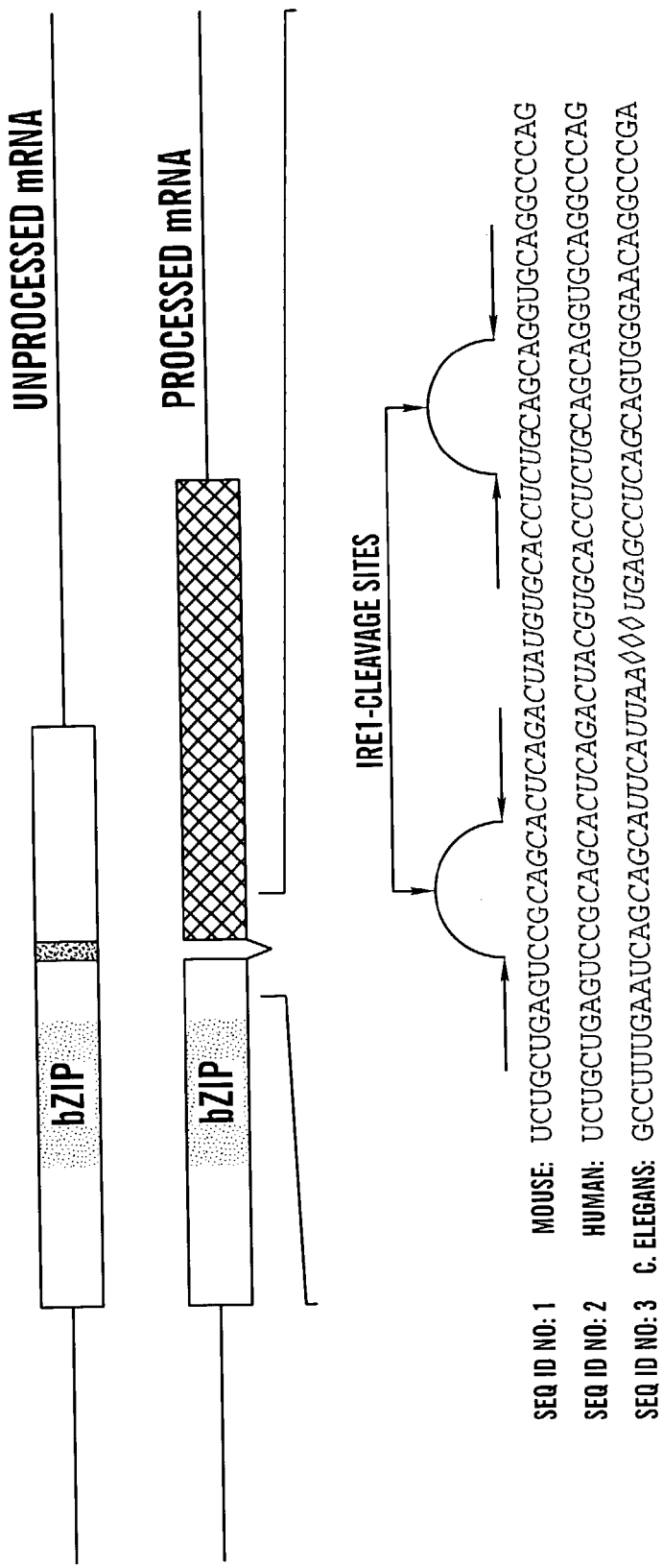
FIG. 2 is a schematic showing the processing of XBP-1 mRNA by IRE1-mediated cleavage and re-ligation changes in the coding region of XBP-1. Expression of the new C-terminal coding region (cross-hatched region above) is completely dependent on IRE1 activity and re-ligation of the mRNA. An antiserum to the peptide encoded by the cross-hatched region and frame of the XBP-1 mRNA would recognize its target only in cells where IRE1 is active and where the ends of the cleaved XBP-1 mRNA can be re-ligated. By fusing any enzyme or other protein marker to the frame in which the cross-hatched region is read, the expression of such a marker becomes subordinate to IRE1 activity and mRNA re-ligation and therefore can report on defects in this process. SEQ ID NO:1, SEQ ID NO:2, and SEQ ID NO:3 depict the RNA sequences surrounding and including the cleaved portion of the XBP-1 mRNA of mouse, human, and *Caenorhabditis elegans*, respectively.

Mammalian lymphocytes are immunized by in vivo immunization of the animal (e.g., a mouse) with the protein or polypeptide of interest (e.g., the unique C-terminal extension of the XBP-1 protein, as described in FIG. 2). Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents (See Milstein and Kohler, *Eur. J. Immunol.* 6:511 (1976), which is hereby incorporated by reference in its entirety). This immortal cell line, which is preferably murine, but may also be derived from cells of other mammalian species, including but not limited, to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering a protein or polypeptide of interest (e.g., the unique C-terminal extension of the XBP-1 protein, as described in FIG. 2) subcutaneously to New Zealand white rabbits which have first been bled to obtain pre-immune serum. The antigens can be injected at a total volume of 100 µl 1 per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbitol 150 mg/Kg IV. This and other procedures for raising polyclonal antibodies are disclosed in E. Harlow, et. al., editors, *Antibodies: A Laboratory Manual* (1988), which is hereby incorporated by reference in its entirety.

In addition to utilizing whole antibodies, the processes of the present invention encompass use of binding portions of such antibodies. Such antibody fragments can be made by conventional procedures, such as proteolytic fragmentation procedures, as described in J. Goding, *Monoclonal Antibodies: Principles and Practice*, pp. 98-118 (N.Y. Academic press 1983), which is hereby incorporated by reference in its entirety.

In another aspect of the present invention, the analyzing step is carried out using such detection methods well known in the art as immunoblotting, ELISA (enzyme-linked immunosorbent assay), or immunochemistry. Other suitable methods involve, for example, a radioimmunoassay, a gel diffusion precipitin reaction assay, an immunodiffusion assay, an agglutination assay, a fluorescent immunoassay, a protein A immunoassay, or an immunoelectrophoresis assay.

In another embodiment of the method of the present invention, an mRNA encoding a marker protein or polypeptide is coupled to translatable and untranslatable XBP-1 mRNA. Such a marker protein or polypeptide acts as a surrogate marker for the activated XBP-1 protein. In this embodiment, determining whether the test compound is effective in inhibiting XBP-1 mRNA processing involves detecting whether the marker protein or polypeptide is present. Test compounds that inhibit the production of the marker protein or polypeptide are considered to have potential effectiveness in treating or preventing a mammalian disease mediated by plasma cells. In one aspect, the marker protein or polypeptide is a reactive enzyme or fluorescent protein. Suitable reactive enzymes include, without limitation, LacZ and alkaline phosphatase. Suitable fluorescent proteins include, without limitation, a green fluorescent protein. However, numerous marker proteins or polypeptides (e.g., reactive enzymes and fluorescent proteins) are well known in the art and are contemplated by the present invention. The precise sequence information on the processing of XBP-1 mRNA by IRE1 permits anyone skilled in the art to produce a reporter gene in which the frame-shift effected by IRE1-mediated XBP-1 splicing leads to the translation of an enzyme (e.g., LacZ or alkaline phosphatase) or fluorescent protein (e.g., green fluorescent protein) that can be detected by established methods (FIG. 2).

Any method of coupling the expression of an easy to detect protein marker to XBP-1 mRNA processing is thus part of this invention.

In yet another embodiment, determining the effectiveness of the test compound to inhibit XBP-1 mRNA processing involves detecting the IRE1 protein in its phosphorylated form is present. In this embodiment, test compounds that inhibit the production of the phosphorylated form of the IRE1 protein have potential effectiveness in treating or preventing a mammalian disease mediated by plasma cells. In one aspect of the present invention, the detecting involves contacting the assay system with antibodies specific to the phosphorylated form of the IRE1 protein and analyzing whether there has been any binding between the antibodies and the phosphorylated form of the IRE1 protein. Because the phosphorylation sites on IRE1 are known, anyone skilled in the art can develop an antiserum or monoclonal antibody to detect the presence of the phosphorylated form of the protein in cells using well established assays (e.g., immunoblot, ELISA, immunochemistry). Thus, use of such assays to screen for inhibitors of IRE1 phosphorylation is contemplated by the present invention. Further, the suitable antibodies and detection methods already described above are useful in this embodiment of the present invention.

In another aspect of the present invention, the assay system for evaluating a test compound's ability to inhibit XBP-1 mRNA processing involves the following components: unprocessed artificial RNA that includes the nucleotide sequence corresponding to untranslatable XBP-1 mRNA, IRE1 protein, and a system suitable to translate translatable XBP-1 mRNA. In this aspect of the present invention, the step of subjecting the test compound to an assay system involves providing a stimulus effective to activate processing of untranslatable XBP-1 mRNA to translatable XBP-1 mRNA with IRE1 present. The step of identifying an effective test compound involves determining whether the test compound is effective in inhibiting the processing of the unprocessed artificial RNA into processed artificial RNA, where the processed artificial RNA involves a nucleotide sequence corresponding to translatable XBP-1 mRNA. One of ordinary skill in the art can produce an artificial RNA substrate that will be accurately cleaved by IRE1 protein in vitro. Any assay to determine if a given compound can inhibit or alter the ability of IRE1 to cleave a natural or artificial RNA substrate is therefore contemplated by the present invention.

The method of the present invention may be used to identify compounds that are effective in treating or preventing mammalian diseases caused by pathogenic immunoglobulins secreted from said plasma cells. Such mammalian diseases include, without limitation, Myasthenia Gravis, Pemphigus Vulgaris, Systemic Lupus Erythromatosus, Guilliain Barré syndrome, proliferative glomerulonephritis, hemophilia with inhibitory antibodies to factor 8, hemophilia with inhibitory antibodies to factor 9, autoimmune thrombocytopenia, autoimmune hemolytic anemia, and paraneoplastic syndrome.

The method of the present invention may also be used to identify compounds that are effective in treating or preventing mammalian diseases such as cancers caused by the abnormal proliferation of plasma cells. Examples of such diseases include, without limitation, Multiple Myeloma, and plasma cell dyscrasia. Because many cancer cells have heightened activity of the signaling pathway initiated by IRE1 (Lee, "The Glucose-Regulated Proteins: Stress Induction and Clinical Applications," *Trends Biochem. Sci.* 26:504-10 (2001), which is hereby incorporated by reference in its entirety), compounds that inhibit IRE1 may have broad utility as anti-cancer agents. Of potential importance in this regard are tumors caused by cells with a very low proliferation index that are not easily killed by the currently used anti-proliferation drugs. An example of such cells are prostate cancer cells.

The present invention also relates to a method of screening a compound for potential effectiveness in treating or preventing a mammalian disease caused by virus infection of mammalian cells. This method involves providing a test compound. The test compound is subjected to an assay system suitable for evaluating the test compound's ability to inhibit processing of untranslatable XBP-1 mRNA to translatable XBP-1 mRNA. The method further involves identifying test compounds that inhibit processing of untranslatable XBP-1 mRNA to translatable XBP-1 mRNA as having potential effectiveness in treating or preventing a mammalian disease caused by virus infection of mammalian cells.

The present invention also relates to a drug useful in treating or preventing a mammalian disease caused by or associated with plasma cells. Examples of such mammalian diseases are described above. In one embodiment, the drug may include a therapeutic compound that inhibits the processing of untranslatable XBP-1 mRNA to translatable XBP-1 mRNA. In one aspect, the therapeutic compound inhibits the IRE1-mediated processing of untranslatable XBP-1 mRNA to translatable XBP-1 mRNA. In another aspect, the therapeutic compound disrupts or interferes with IRE1's ability to recognize an accumulation of protein load in the endoplasmic reticulum of a mammalian cell. An example of a suitable mammalian cell includes, without limitation, a developing plasma cell. In another aspect, the therapeutic compound disrupts or interferes with IRE1's ability to undergo self-association. In another aspect, the therapeutic compound disrupts or interferes with IRE1's ability to undergo phosphorylation. In yet another aspect, the therapeutic compound promotes the dephosphorylation of IRE1. In still yet another aspect, the therapeutic compound blocks the ability of IRE1 phosphorylation to promote the cleavage of untranslatable XBP-1 mRNA. In another aspect, the therapeutic compound blocks the cleavage reaction of untranslatable XBP-1 mRNA by IRE1. In yet another aspect, the therapeutic compound distorts the cleavage reaction of untranslatable XBP-1 mRNA by IRE1 so that the cleaved XBP-1 mRNA no longer encodes an active XBP-1 protein. In a further aspect, the therapeutic compound interferes with the ligation of two ends of a cleaved XBP-1 mRNA such that the two ends are not joined together or are joined together improperly, resulting in an XBP-1 mRNA that is unable to be translated into an active XBP-1 protein.

The present invention also relates to a method of treating or preventing a mammalian disease in an individual caused by the secretion of pathogenic immunoglobulins from plasma cells. This method involves administering to the individual an effective amount of a drug according to the present invention. The method may be used to treat or prevent such mammalian diseases as Myasthenia Gravis, Pemphigus Vulgaris, Systemic Lupus Erythromatosus, Guilliain Barré syndrome, proliferative glomerulonephritis, hemophilia with inhibitory antibodies to factor 8, hemophilia with inhibitory antibodies to factor 9, autoimmune thrombocytopenia, autoimmune hemolytic anemia, and paraneoplastic syndrome.

The present invention also relates to a method of treating or preventing a mammalian disease in an individual caused by the abnormal proliferation of plasma cells. This method involves administering to the individual an effective amount of a drug according to the present invention. This method may be used to treat or prevent such mammalian diseases as Multiple Myeloma and plasma cell dyscrasia.

The present invention also relates to a method of treating or preventing a condition in an individual mediated by the processing of untranslatable XBP-1 mRNA to translatable XBP-1 mRNA. This method involves administering to the individual an effective amount of the drug according to the present invention.

In one aspect, the step of administering an effective amount of the drug according to the present invention (as described above for the methods of treating or preventing various types of diseases) may involve administering the drug orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing a therapeutic compound that inhibits the processing of untranslatable XBP-1 mRNA to translatable XBP-1 mRNA and a carrier, for example, lubricants and inert fillers such as, lactose, sucrose, or cornstarch. In another embodiment, these therapeutic compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

In another one aspect, the drugs containing the therapeutic compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, the drugs of the present invention may be incorporated with excipients and used in the form of tablets, capsules, elixirs, suspensions, syrups, and the like. In one aspect, such drugs should contain at least 0.1% of the therapeutic compound of the present invention. The percentage of the therapeutic compound in the drugs of the present invention may, of course, be varied and may conveniently be between about 2% to about 60% of the weight of the unit. The amount of active therapeutic compound in the drugs of the present invention is such that a suitable dosage will be obtained. As one example, drugs according to the present invention are prepared so that an oral dosage unit contains between about 1 and 250 mg of therapeutic compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

As described above, in one aspect of the present invention, the drugs containing the therapeutic compounds may be administered parenterally. Solutions or suspensions of the therapeutic compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The drugs containing the therapeutic compounds of the present invention may also be administered directly to the airways in the form of an aerosol. For use as aerosols, the therapeutic compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The present invention also relates to a method of detecting the activity of XBP-1 in living cells. This method involves providing a living cell transfected with an artificial XBP-1/reporter gene. A suitable artificial XBP-1/reporter gene may include a coding region for untranslatable XBP-1 and a reporter gene. The living cell is provided under conditions effective to allow the reporter gene to express a reporter protein or polypeptide product only when untranslatable XBP-1 is processed into translatable XBP-1. In this method, the living cell is contacted with an endoplasmic reticulum stress-inducing agent under conditions effective to activate processing of untranslatable XBP-1 mRNA to translatable mRNA. The method further involves detecting the presence of the protein or polypeptide product of the reporter gene in the living cells using an assay system. The presence of the protein or polypeptide product indicates activity of XBP-1 in the living cells.

As used herein, a "reporter" gene is a gene that (1) is expressed only when translatable XBP-1 mRNA is produced and (2) encodes a gene product that can be detected or selected for. Examples of suitable assay systems include, without limitation, immunoblotting, an ELISA, and immunochemistry. In addition, suitable protein or polypeptide products of the reporter gene include, without limitation, a green fluorescent protein (GFP), β-galactosidase, secreted alkaline phosphatase (SEAP), chloramphenicol acetyltransferase (CAT), Luciferase, human growth hormone, and neomycin phosphotransferase.

EXAMPLES

Example 1

IRE1 Couples Endoplasmic Reticulum Load to Secretory Capacity by Processing the XBP-1 mRNA The unfolded protein response (UPR) matches the folding capacity of the endoplasmic reticulum (ER) to the load of client proteins in the organelle (Mori, "Tripartite Management of Unfolded Proteins in the Endoplasmic Reticulum," *Cell* 101:451-454 (2000); Kaufman, "Stress Signaling From the Lumen of the Endoplasmic Reticulum: Coordination of Gene Transcriptional and Translational Controls," *Genes Dev.* 13:1211-1233 (1999), which are hereby incorporated by reference in their entirety). Processing of HAC1 mRNA by activated Ire1p leads to synthesis of the transcription factor Hac1p and activation of the UPR in yeast (Shamu, "Splicing: HACking into the Unfolded-Protein Response," *Curr. Biol.* 8:R121-123 (1998), which is hereby incorporated by reference in its entirety). The responses to activated IRE1 in metazoans are less well understood. It was found that mutations in either ire-1 or the transcription factor-encoding xbp-1 gene abolished the UPR in *C. elegans*. Mammalian XBP-1 is essential for immunoglobulin secretion and plasma cell development (Reimold et al., "Plasma Cell Differentiation Requires the Transcription Factor XBP-1," *Nature* 412:300-307 (2001), which is hereby incorporated by reference in its entirety) and high levels of XBP-1 mRNA are found in specialized secretory cells (Clauss et al., "In Situ Hybridization Studies Suggest a Role for the Basic Region Leucine Zipper Protein hXBP-1 in Exocrine Gland and Skeletal Development During Mouse Embryogenesis," *Dev. Dyn.* 197:146-156 (1993), which is hereby incorporated by reference in its entirety). Activation of the UPR causes IRE1-dependent splicing of a small intron from the XBP-1 mRNA both in *C. elegans* and mouse. The protein encoded by the processed murine XBP-1 mRNA accumulated during the UPR whereas that encoded by the unprocessed mRNA did not. Purified mouse IRE1 accurately cleaved XBP-1 mRNA in vitro, indicating that XBP-1 is a direct target of IRE1 endonucleolytic activity. The findings suggest that physiological ER load regulates a developmental decision in higher eukaryotes.

Example 2

Analysis of the UPR in *C. elegans*

A 1.1 kilobase (Kb) fragment of *C. elegans* genomic DNA immediately 5' of the predicted initiation ATG of hsp-4 was amplified by PCR and ligated in-frame with GFP in the plasmid pPD95.75 (gift of Andy Fire, Carnegie Institute of Washington). The hsp-4::gfp(zcIs4) V strain was generated by co-injecting the hsp-4::gfp clone with the lin-15 rescuing plasmid, pSK1 (Clark et al., "The *Caenorhabditis elegans* Locus Lin-15, a Negative Regulator of a Tyrosine Kinase Signaling Pathway, Encodes Two Different Proteins," *Genetics* 137:987-997 (1994), which is hereby incorporated by reference in its entirety), into lin-15(n765ts) animals and then integrating the extrachromosomal array with ultraviolet/trimethylpsoralen (UV/TMP) treatment. The F2 progeny of ethylmethane sulphonate (EMS)-treated hsp-4::gfp(zcIs4)V animals were screened for mutants with high levels of GFP expression to identify mutations that constitutively induce the UPR. Several mutations were recovered, including upr-1 (zc6)X, which induced a high level of GFP expression in the posterior gut. To isolate mutations that blocked hsp-4::gfp induction, the F2 progeny of EMS-treated hsp-4::gfp(zcIs4) V; upr-1(zc6)X animals were screened for mutants with a reduced GFP signal. The mutations were mapped using standard methods.

RNAi was performed by injecting double-stranded RNA made in vitro using as a template the 720 bp SalI/EcoRI fragment of the ire-1 cDNA (clone yk8e9) or the 515 bp SalI/NcoI fragment of the xbp-1 cDNA (clone yk146d1) into young adult hermaphrodites and then observing the phenotype of the F1 progeny as described previously (Fire et al., "Potent and Specific Genetic Interference by Double-Stranded RNA in *Caenorhabditis elegans*," *Nature* 391:806-811 (1998), which is hereby incorporated by reference in its entirety). Animals were transferred to plates containing 5 µg/ml tunicamycin (Calbiochem) and visualized the GFP expression using an epifluorescent stereomicroscope (Zeiss M2 Bio). RNA for Northern blot analysis was isolated by acid-guanidinium thiocyanate-phenol-chloroform extraction. A radiolabeled 100 bp HindIII/XhoI fragment from hsp-4 cDNA clone yk34e10 was used as a probe.

Example 3

Cell Culture, Transfection, Immunoblot and Immunoprecipitation

Mouse embryonic fibroblasts and ES cells lacking IRE1 activity (IRE1α-/- or IRE1α, IRE1β-/-) and PERK-/-fibroblasts were cultured as previously described (Harding et al., "Regulated Translation Initiation Controls Stress-Induced Gene Expression in Mammalian Cells," *Mol. Cell* 6:1099-1108 (2000); and Urano et al., "Coupling of Stress in the Endoplasmic Reticulum to Activation of JNK Protein Kinases by Transmembrane Protein Kinase IRE1," *Science* 287:664-666 (2000), which are hereby incorporated by reference in their entirety). Cells were treated with tunicamycin (2.5 µg/ml, Calbiochem), thapsigargin (100 nM, Sigma), dithiothreitol (2 mM, Sigma) or the proteasome inhibitor MG132 (25 µM, Calbiochem) as indicated. To prepare B-cell blasts, cells were teased from crushed adult mouse spleen and cultured in the presence of 25 µg/ml *E. coli* lipopolysaccharide.

A full-length murine XBP-1 cDNA was purchased (EST BF454459, Research Genetics). The processed version of the cDNA was created by replacing the XhoI-EcoRV fragment of the unprocessed cDNA with the equivalent fragment from the processed cDNA obtained by RT-PCR of mRNA from stressed cells. FLAG-tagged versions of the two cDNAs were constructed by inserting the FLAG epitope tag sequence immediately 3' of the ATG start codon and the cDNAs were expressed from a plasmid containing the human cytomegalovirus virus (CMV) promoter (pFlag-CMV2).

XBP-1 proteins in whole cell extracts were detected by immunoblot of 9% PAGE-SDS using a rabbit polyclonal serum directed to residues 97-267 common to both 54 kDa and 33 kDa XBP-1 proteins (sc-7160, Santa Cruz Biotechnology). XBP-1 proteins in transfected cells were detected by a monoclonal antibody to the FLAG epitope tag (Kodak-IBI). CREB and CHOP were detected as described previously (Harding et al., "Regulated Translation Initiation Controls Stress-Induced Gene Expression in Mammalian Cells," *Mol. Cell* 6:1099-1108 (2000), which is hereby incorporated by reference in its entirety).

Newly synthesized proteins were labeled in vivo with $^{35}$S-methionine and $^{35}$S-cysteine (500 µCi/ml, Translabel, ICN Biochemicals). After removal of the labeling media cells were washed and incubated in complete media for coldchase. Labeled XBP-1 proteins from whole cell extracts prepared in radio-immunoprecipitation buffer (Harding et al., "Regulated Translation Initiation Controls Stress-Induced Gene Expression in Mammalian Cells," Mol. Cell 6:1099-1108 (2000), which is hereby incorporated by reference in its entirety) were immunoprecipitated using the anti-Flag or anti XBP-1 antibodies described above and revealed by autoradiography after 9% PAGE-SDS. Incorporation of radiolabel was quantified by phosphoimager analysis. In calculating the relative synthesis rates of 54 kDa XBP-1 and 33 kDa XBP-1 the relative incorporation of label was corrected for differences in the content of methionine (7:6) and cysteine (4:3) predicted for the two proteins.

Example 4

Analysis of XBP-1 mRNA Cleavage by IRE1

RNA from untreated and tunicamycin-treated wildtype and IRE1α–/– mouse ES cells was reverse transcribed using an XBP-1 specific antisense primer, mXBP1.4AS: 5'-GCACCTTCTAGAAGCTACACTAGCA-3' (SEQ ID NO:5). Nested PCR using the sense primer mXBP1.3S (5'-AAACAGAGTAGCAGCGCAGACTGC-3') (SEQ ID NO:6) and the antisense primer mXBP1.2AS: (5'-GGATCTCTAAAACTAGAGGCTTGGTG-3') (SEQ ID NO:7) amplified a 600 bp cDNA product encompassing the IRE1-cleavage sites. This fragment was further digested by PstI to reveal a restriction site that is lost following IRE1-mediated cleavage and splicing of the mRNA. The cDNA fragments were resolved on a 2% agarose gel and revealed by Southern blot hybridized to the $^{32}$P-labeled XhoI-PstI fragment of the unprocessed XBP-1 cDNA. The processed cDNAs from mouse and *C. elegans* were sequenced and the sequence deposited in Genebank under accession numbers AF443 192 and AF443 191, respectively.

The XhoI-EcoRV fragment of the XBP-1 cDNA from unstressed (XBP-1$^{uP}$) and stressed (XBP-1$^{Pr}$) mouse ES cells was ligated into pBluscript plasmid (Stratagene) and sense strand $^{32}$P-labeled RNA was transcribed in vitro using a kit from Promega. The labeled RNA was incubated in the presence or absence of 1 mM ATP with the recombinant cytoplasmic domain of IRE1β purified from SF9 cells as described (Niwa et al., "A Role for Presenilin-1 in Nuclear Accumulation of Ire1 Fragments and Induction of the Mammalian Unfolded Protein Response," Cell 99:691-702 (1999), which is hereby incorporated by reference in its entirety). The radiolabeled RNA fragments were resolved on 8M urea 6% PAGE gel and revealed by autoradiography.

Example 5

Mapping the In Vitro Cleavage of Mouse XBP-1 by IRE1

The XhoI-EcoRV fragment of the XBP-1 cDNA from unstressed (XBP-1$^{uP}$) and stressed (XBP-1$^{Pr}$) mouse ES cells was ligated into pBluescript plasmid (Stratagene) which was then linearized with EcoR1 and sense strand $^{32}$p-labeled RNA was transcribed in vitro using a kit from Promega. The labeled RNA was incubated in the presence or absence of 1 mM ATP with the recombinant cytoplasmic domain of IRE1β purified from SF9 cells as described (Niwa et al., "A Role for Presenilin-1 in Nuclear Accumulation of Ire1 Fragments and Induction of the Mammalian Unfolded Protein Response," Cell 99:691-702 (1999), which is hereby incorporated by reference in its entirety). The radiolabeled RNA fragments were resolved on 8M urea 6% PAGE gel and revealed by autoradiography. To generate a sequencing ladder with nested fragments having the same ends as the labeled RNA fragments, a primer was designed that annealed to the pBluescript plasmid containing the aforementioned XhoI-EcoRV fragment of the XBP-1 cDNA at the predicted 5' overhang generated by EcoRI digestion. The $^{32}$P-radiolabeled primer was used for both dideoxy-nucleotide sequencing of the plasmid and for primer extension of the in vitro digested XBP-1 mRNA.

Example 6

Measuring the Half-Life of Endogenous XBP-1 pr

Cells were left untreated or pretreated for 3 hours with tunicamycin (2.5 µg/ml), followed by a short 10 minute labeling pulse and a chase of 30 and 60 minutes. Endogenous XBP-1 protein was immunoprecipitated using the rabbit anti-XBP-1 serum described above.

IRE1 is an ER resident stress activated endonuclease conserved in all known eukaryotes. In yeast, Ire1p-mediated unconventional splicing of an intron from the HAC1 mRNA controls the expression of the encoded transcription factor (Shamu, "Splicing: HACking into the Unfolded-Protein Response," Curr. Biol. 8:R121-123 (1998), which is hereby incorporated by reference in its entirety) and is required for upregulation of most UPR target genes (Travers et al., "Functional and Genomic Analyses Reveal an Essential Coordination Between the Unfolded Protein Response and ER-Associated Degradation," Cell 101:249-258 (2000); and Casagrande et al., "Degradation of Proteins From the ER of *S. Cerevisiae* Requires an Intact Unfolded Protein Response Pathway," Mol. Cell 5:729-735 (2000), which are hereby incorporated by reference in their entirety). UPR gene expression in mammals largely relies on PERK and ATF6 (Scheuner et al., "Translational Control is Required For the Unfolded Protein Response and In-Vivo Glucose Homeostasis," Mol. Cell 7:1165-1176 (2001); Harding et al., "Regulated Translation Initiation Controls Stress-Induced Gene Expression in Mammalian Cells," Mol. Cell 6:1099-1108 (2000), which is hereby incorporated by reference; Yoshida et al., "ATF6 Activated by Proteolysis Binds in the Presence of NF-Y (CBF) Directly to the Cis-Acting Element Responsible for the Mammalian Unfolded Protein Response," Mol. Cell. Biol. 20:6755-6767 (2000); and Ye et al., "ER Stress Induces Cleavage of Membrane-Bound ATF6 by the Same Proteases that Process SREBPs," Mol. Cell 6:1355-1364 (2000), which are hereby incorporated by reference in their entirety), which are absent from yeast. Furthermore, mammalian IRE1s activate JUN N-terminal kinase by recruiting the TRAF2 protein to the ER membrane independently of their endonucleolytic activity (Urano et al., "Coupling of Stress in the Endoplasmic Reticulum to Activation of JNK Protein Kinases by Transmembrane Protein Kinase IRE1," Science 287:664-666 (2000), which is hereby incorporated by reference in its entirety). It was unclear therefore whether IRE1s of higher eukaryotes also signal through processing of HAC1-like mRNA targets. To address this issue, a genetic strategy was employed to identify UPR regulatory genes in *C. elegans*, a simple organism whose genome is predicted to encode homologues of all three known proximal, stress-sensing components of the metazoan UPR: IRE1, PERK and ATF6.

Figure 3A:
FIGS. 3A-3J demonstrate the identification of mutants in the *C. elegans* unfolded protein response (UPR).
Figure 3B:
Figure 3C:
Figure 3D:

*C. elegans* has two homologues of the ER chaperone BiP, hsp-3 and hsp-4. An hsp-4::gfp transcriptional reporter had relatively low basal GFP expression (most prominent in the spermatheca, FIG. 3A) but expression was strongly induced in the gut and hypodermis following treatment with the ER stress inducer tunicamycin (FIG. 3B). Inactivation of ire-1 function by RNAi blocked both basal and inducible hsp-4::gfp expression (FIG. 3C), suggesting that ire-1 signaling is required for hsp-4 induction in *C. elegans*, as it is in yeast. To identify genes needed for the UPR, mutations that blocked the induction of the hsp-4::gfp reporter were sought. Because treatment with tunicamycin occasionally produced variable and incomplete hsp-4::gfp induction, several mutations were first isolated that constitutively activated hsp-4::gfp expression, presumably by causing ER stress. One semi-dominant mutation, upr-1(zc6)X, (unfolded protein response-1) uniformly activated hsp-4::gfp in the posterior gut (FIG. 3D). Ire-1 RNAi was confirmed to suppress hsp-4::gfp activation by upr-1(zc6)X and then screened for mutations that blocked this activation.

Figure 3E:
Figure 3F:
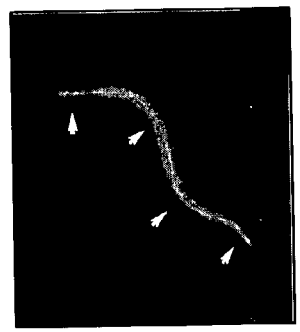
Figure 3G:
Figure 3H:
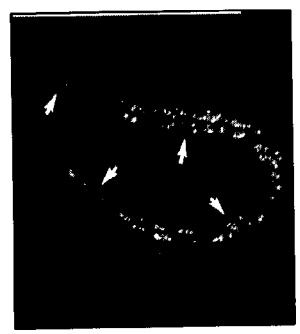
Figure 3I:
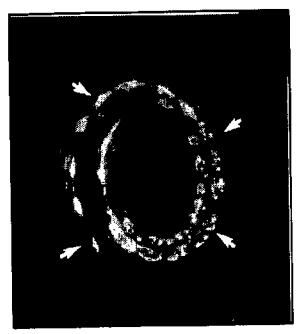

Four allelic mutations that impaired hsp-4::gfp induction were found in ire-1 (FIGS. 3E, 3F and 3J): zc10 and zc11 alter the 3' splice acceptor site of intron 2 and zc13 (G702D) and zc14 (G739R) are missense mutations that affect conserved residues in the kinase domain. A fifth mutation, zc12, that strongly blocked hsp-4::gfp gene induction (FIGS. 3G, 3H and 3J) mapped to the interval between cosmid F34D10 and dpy-17 on chromosome III. A plausible candidate for a downstream target of ire-1, a predicted bZIP transcription factor gene, R74.3, was located in this interval. Sequence analysis revealed a single nonsense mutation at residue 11 in the predicted R74.3 protein in zc12 mutants and RNAi of R74.3 inhibited hsp-4::gfp induction (FIG. 3I). Together, these results indicate that R74.3 has an essential role in the *C. elegans* UPR.

Figure 4A:
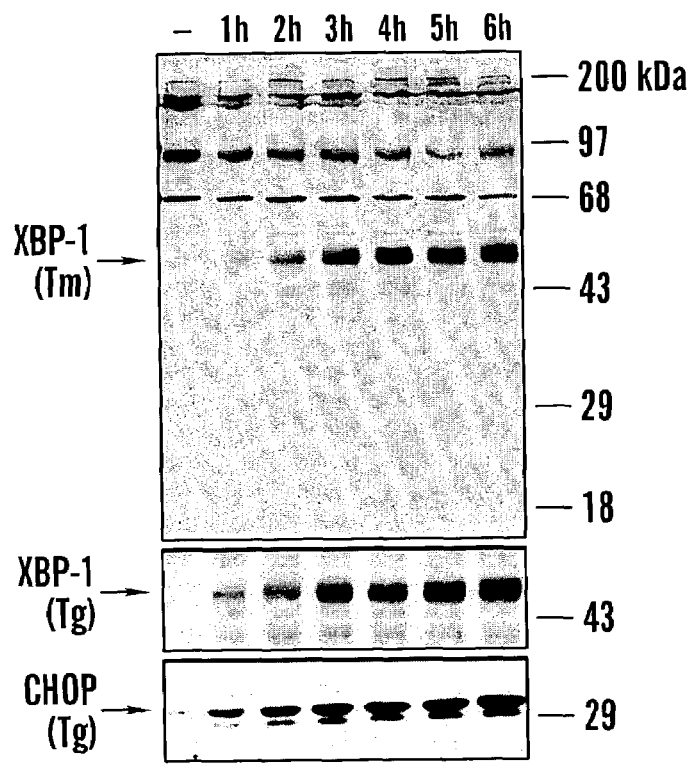
FIGS. 4A-4C are immunoblots showing mammalian XBP-1 expression during ER stress is IRE-1 dependent.
Figure 4B:
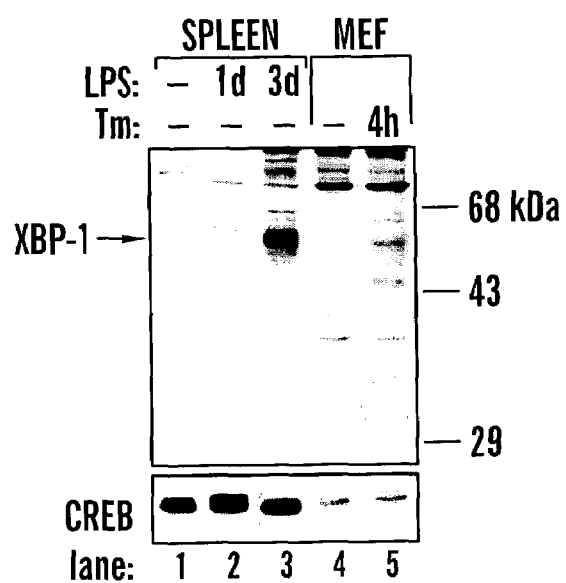

The predicted R74.3 protein is most similar to mouse XBP-1, which has been shown to bind the BiP ER stress response element (Yoshida et al., "Identification of the Cis-Acting Endoplasmic Reticulum Stress Response Element Responsible for Transcriptional Induction of Mammalian Glucose-Regulated Proteins. Involvement of Basic Leucine Zipper Transcription Factors," *J. Biol. Chem.* 273:33741-33749 (1998), which is hereby incorporated by reference in its entirety). Therefore, the regulation of XBP-1 in the mammalian UPR was further investigated. ER stress induced a 54 kDa protein strongly reactive with antiserum to XBP-1 (FIG. 4A). The 54 kDa XBP-1 protein was also induced during the in vitro differentiation of B-cells to plasma cells by exposure to bacterial lipopolysaccharide (FIG. 4B). Thus, ER stress and differentiation-induced remodeling of the secretory apparatus are both associated with XBP-1 expression.

Figure 4C:
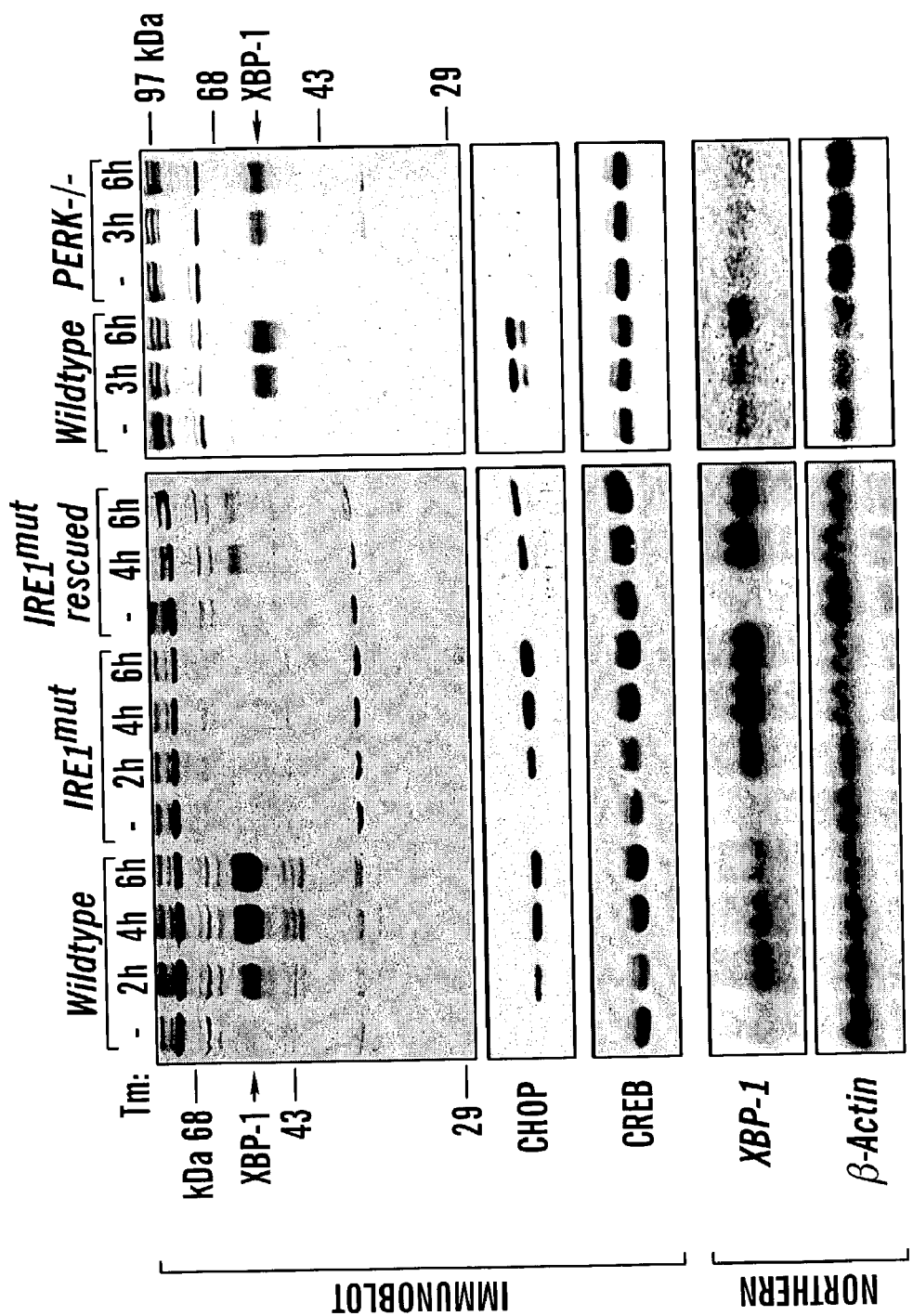

Mice have two IRE1 genes: IRE1α is essential for viability and broadly expressed (Urano et al., "Coupling of Stress in the Endoplasmic Reticulum to Activation of JNK Protein Kinases by Transmembrane Protein Kinase IRE1," *Science* 287:664-666 (2000); and Tirasophon et al., "A Stress Response Pathway From the Endoplasmic Reticulum to the Nucleus Requires a Novel Bifunctional Protein Kinase/Endoribonuclease (Ire1p) in Mammalian Cells," *Genes Dev.* 12:1812-1824 (1998), which are hereby incorporated by reference in their entirety) and IRE1β is only expressed in the gastrointestinal mucosa (Bertolotti et al., "Increased Sensitivity to Dextran Sodium Sulfate Colitis in IRE1b Deficient Mice," *J. Clin. Invest.* 107:585-593 (2001); Wang et al., "Cloning of Mammalian Ire1 Reveals Diversity in the ER Stress Responses," *EMBO J.* 17:5708-5717 (1998), which are hereby incorporated by reference in their entirety). Induction of the 54 kDa XBP-1 protein by ER stress was not observed in fibroblasts lacking IRE1 gene function (IRE1α-/- or IRE1αβ-/-) but could be rescued by introduction of an IRE1 transgene (FIG. 4C). ER stress has been shown to increase XBP-1 mRNA levels (10-). However, IRE1 mutant cells that do not express the 54 kDa XBP-1 had higher levels of XBP-1 mRNA than wildtype cells (FIG. 4C, lower panels). Furthermore, PERK-/- cells that failed to induce XBP-1 mRNA, nonetheless accumulate 54 kDa XBP-1 protein when stressed (albeit to lower levels than wildtype cells, FIG. 4C). IRE1 activity is thus required for XBP-1 protein expression, whereas ER-stress mediated increase in XBP-1 mRNA is less important in this process.

Figure 5A:
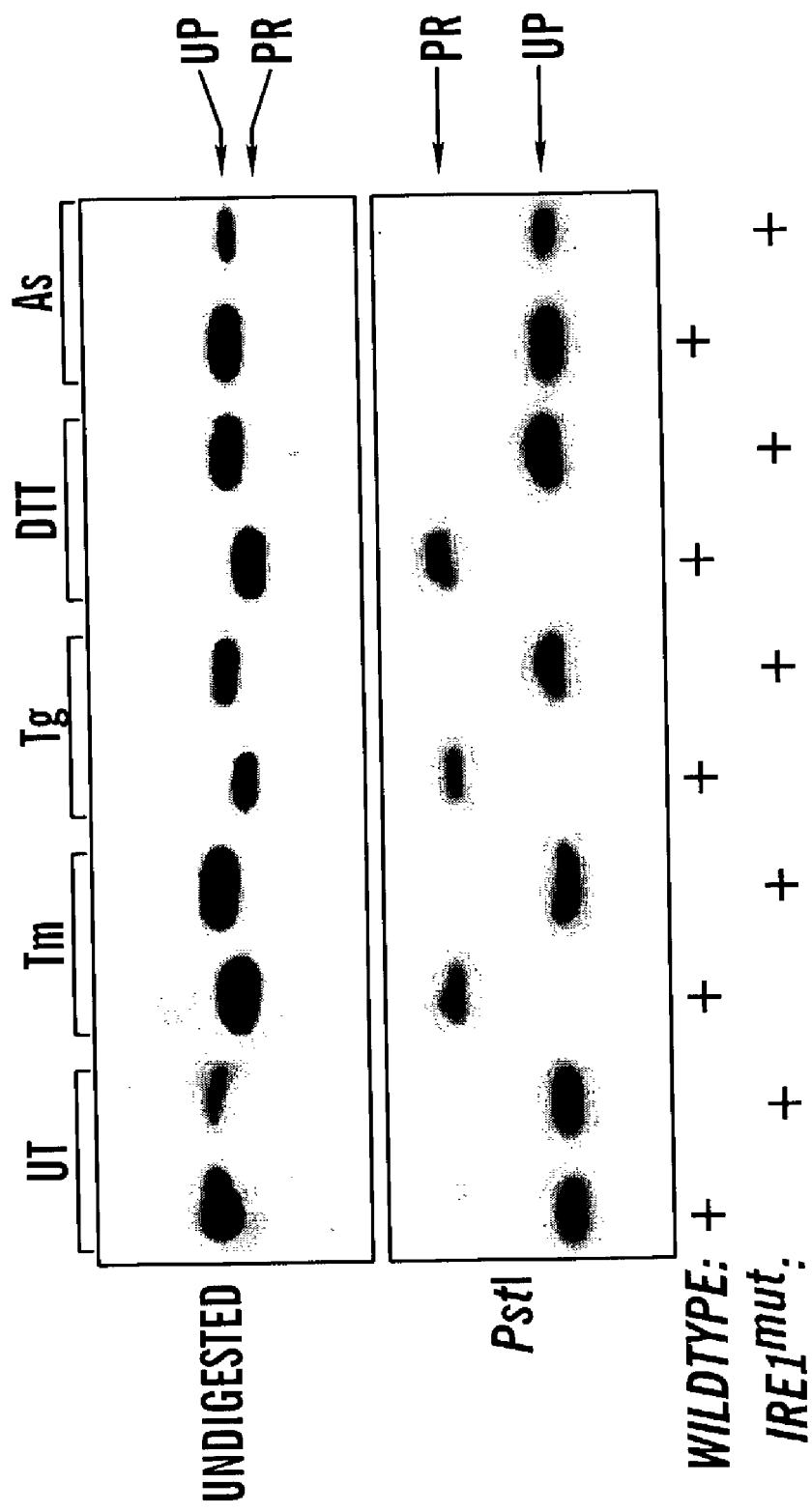
FIGS. 5A-5E show diagrams demonstrating the IRE1-mediated processing of XBP-1 mRNA.
Figure 5B:
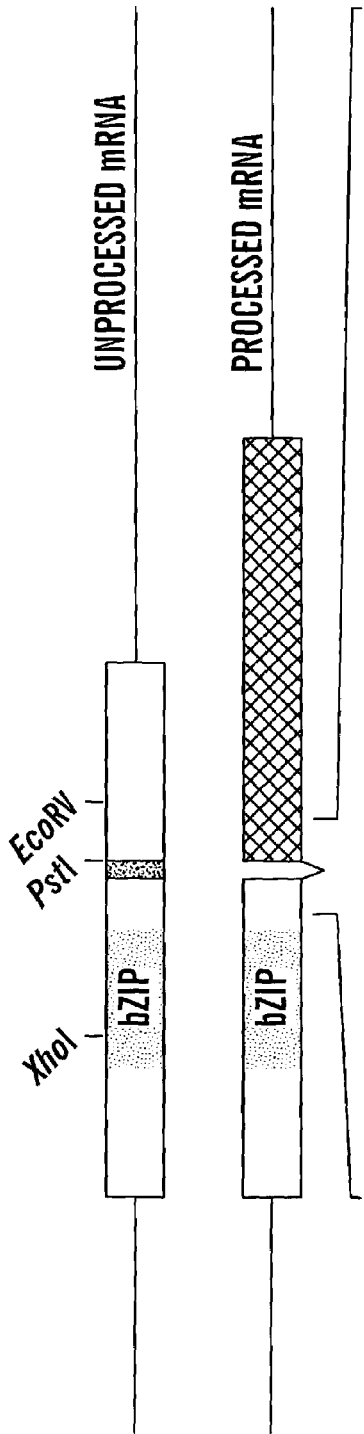
Figure 5C:
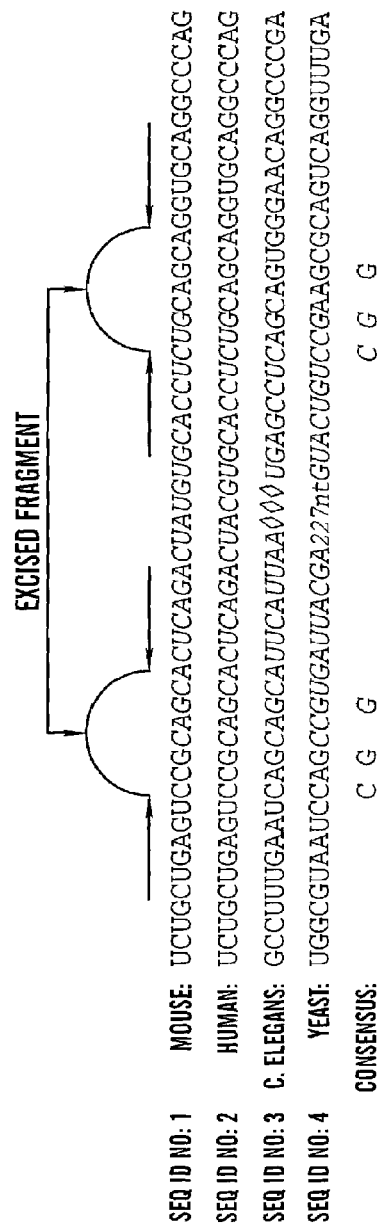
Figure 5E:
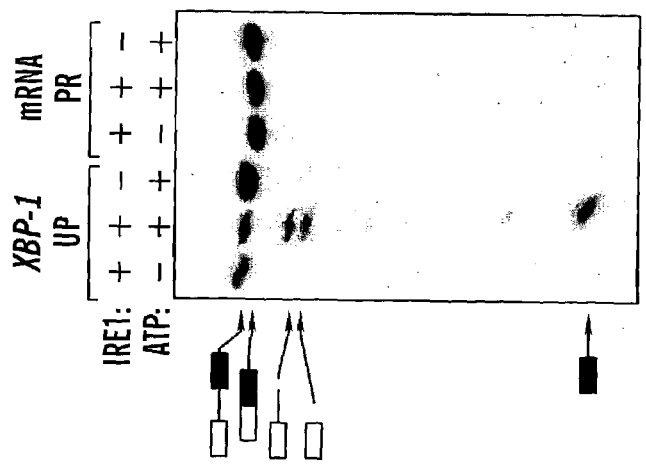
Figure 5D:
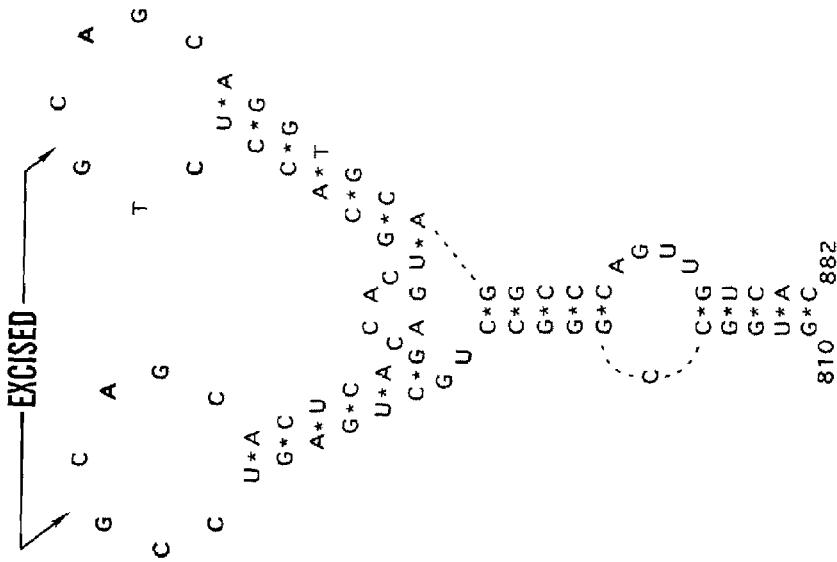

To investigate possible IRE1 mediated processing of the XBP-1 mRNA, RT-PCR was performed of XBP-1 mRNA from unstressed and stressed wildtype and IRE1 mutant mouse cells. A consistent IRE1 and ER stress-dependent decrease in the size of the XhoI-EcoRV fragment of the XBP-1 cDNA was found (FIG. 5A). Sequencing revealed excision of a 26 nucleotide intron from the XBP-1 cDNA derived from stressed wildtype cells (FIGS. 5B and 5C). A similarly located 23 nucleotide intron was removed by ER stress from the *C. elegans* R74.3 mRNA (FIG. 5C). The boundaries of these introns were encompassed in a predicted RNA structure that included two loops of 7 residues held in place by short stems (FIGS. 5C and 5D). The sequence of the loops corresponded perfectly to the empirically-defined consensus for cleavage of yeast HAC1 mRNA by Ire1p (Gonzalez et al., "Mechanism of Non-Spliceosomal mRNA Splicing in the Unfolded Protein Response Pathway," *EMBO J.* 18:3119-3132 (1999); and Kawahara et al., "Unconventional Splicing of HAC1/ERN4 mRNA Required for the Unfolded Protein Response. Sequence-Specific and Non-Sequential Cleavage of the Splice Sites," *J. Biol. Chem.* 273:1802-1807 (1998), which are hereby incorporated by reference in their entirety). The RNA sequences 5' and 3' of these two putative processing sites are predicted to form extensive base-pair interactions that could hold together the cleaved ends of the mRNA (FIG. 5D), as has been predicted for the HAC1 mRNA (Gonzalez et al., "Mechanism of Non-Spliceosomal mRNA Splicing in the Unfolded Protein Response Pathway," *EMBO J.* 18:3119-3132 (1999), which is hereby incorporated by reference in its entirety).

Figure 6:
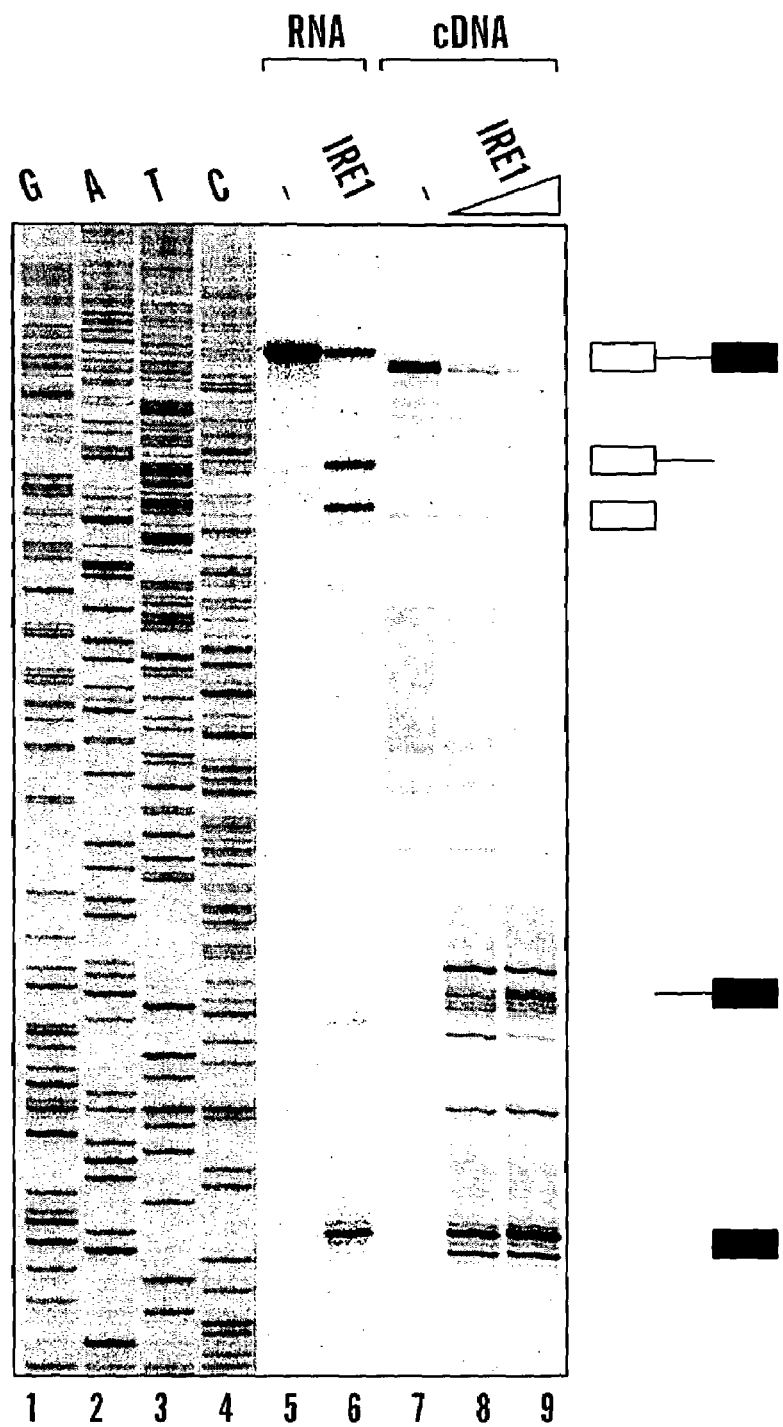
FIG. 6 is an autoradiogram demonstrating the mapping of the in vitro cleavage of mouse XBP-1 by IRE1. Autoradiogram of a sequencing gel on which the uncleaved and cleaved mRNA (prepared as for FIG. 5E) were resolved (lanes 5 and 6) alongside a cDNA sequencing ladder commencing at the 3' end of the labeled mRNA (lanes 1-4). Primer extension of the uncleaved mRNA (lane 7) or cleaved mRNA (lanes 8 and 9) with the same radiolabeled primer used to generate the sequencing ladder shown in lanes 1-4.

To study the role of IRE1 in processing of the XBP-1 mRNA, the cleavage event was reconstructed in vitro. The cytoplasmic effector domain of murine IRE1β was purified from insect cells and reacted in vitro with radiolabeled transcribed unprocessed XBP-1 mRNA (XBP-1$^{up}$) or with XBP-1 mRNA transcribed from a processed cDNA template (XBP-1$^{pr}$). IRE1β efficiently cleaved XBP-1$^{up}$ RNA in an ATP-dependent manner but did not cleave XBP-1$^{pr}$ (FIG. 5E). The location of the in vitro cleavage sites was mapped by primer extension and found to coincide with the sites utilized in vivo (FIG. 6).

Re-ligation of XBP-1 mRNA following removal of this 26 nucleotide intron results in a shift of the reading frame and continuation of the protein coding region into the former 3' UTR (FIG. 5B). The protein predicted by the extended open reading frame of the processed XBP-1 mRNA (XBP-1$^{pr}$) is similar in size to the 54 kDa XBP-1 protein detected in stressed cells. To explore further the relationship between processing of the XBP-1 mRNA and expression of the 54 kDa protein, both processed and unprocessed XBP-1 cDNAs were modified to encode N-terminal FLAG epitope-tagged proteins and studied their expression in transfected cells. HEK 293T cells transfected with the processed XBP-1 cDNA constitutively expressed high levels of the 54 kDa XBP-1 protein (FIG. 7A). By contrast, cells transfected with XBP-1$^{up}$ expressed only low levels of a FLAG-tagged 33 kDa protein, consistent in size with the open reading frame specified by the unprocessed mRNA. Upon treatment with tunicamycin, cells transfected with the XBP-1$^{up}$ expressed high levels of FLAG-tagged 54 kDa protein (FIG. 7A). These observations indicate that the protein encoded by the unprocessed mRNA was poorly expressed and that processing of the exogenous mRNA by endogenous IRE1 led to the expression of 54 kDa XBP-1.

Figures 7C, 7D:
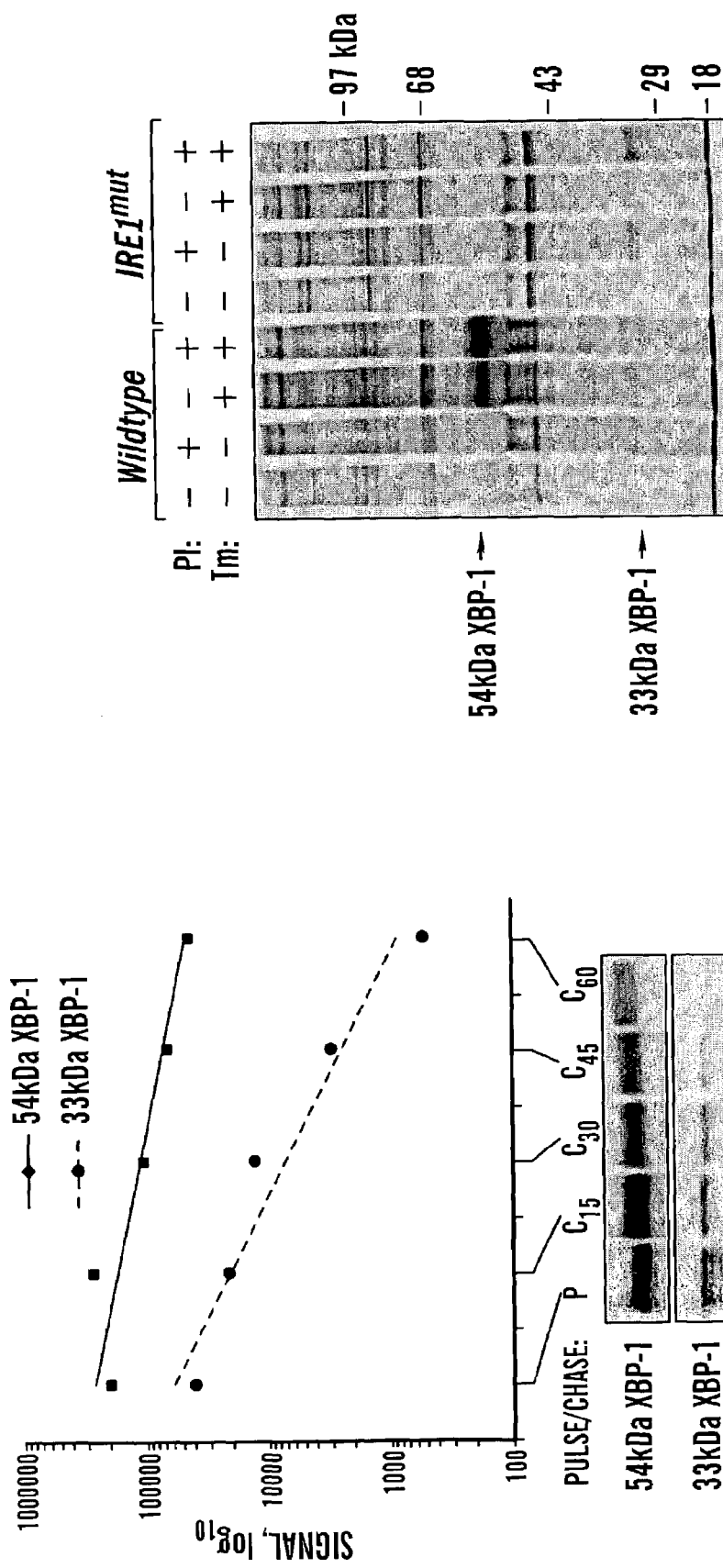

Pulse-chase experiments were performed to explore the basis of the differences in expression of proteins encoded by the transfected XBP-1$^{up}$ and XBP-1$^{pr}$ mRNAs, as Northern blot analysis showed similar levels of the two mRNAs (FIG. 7B). The 54 kDa XBP-1 protein accumulated to 4 fold higher level than 33 kDa XBP-1, following a short (10-minute) labeling pulse and the half life of 54 kDa XBP-1 was twice that of 33 kDa XBP-1 (22 minutes and 11 minutes, respectively). Based on these measurements, the synthesis of 54 kDa XBP-1 protein is calculated to be ~3-fold higher than that of 33 kDa XBP-1. Endogenous 54 kDa XBP-1 also accumulated to high levels in pulse-labeled tunicamycin-treated wildtype cells whereas labeled 33 kDa XBP-1 protein was barely detectable (FIG. 7D). The 33 kDa XBP-1 signal was more obvious in IRE1 mutant cells, presumably because they accumulate XBP-1$^{up}$ mRNA (FIG. 4C). Levels of 33 kDa XBP-1 protein increased further in cells treated with a proteasome inhibitor (FIG. 7D and FIG. 8), consistent with the short half life of protein. The half-life of endogenous 54 kDa XBP-1 was ~21 minutes, similar to that of the over-expressed protein whereas the weak incorporation of label precluded accurate measurement of the half-life of endogenous 33 kDa XBP-1 protein (FIG. 8).

Figure 3J:
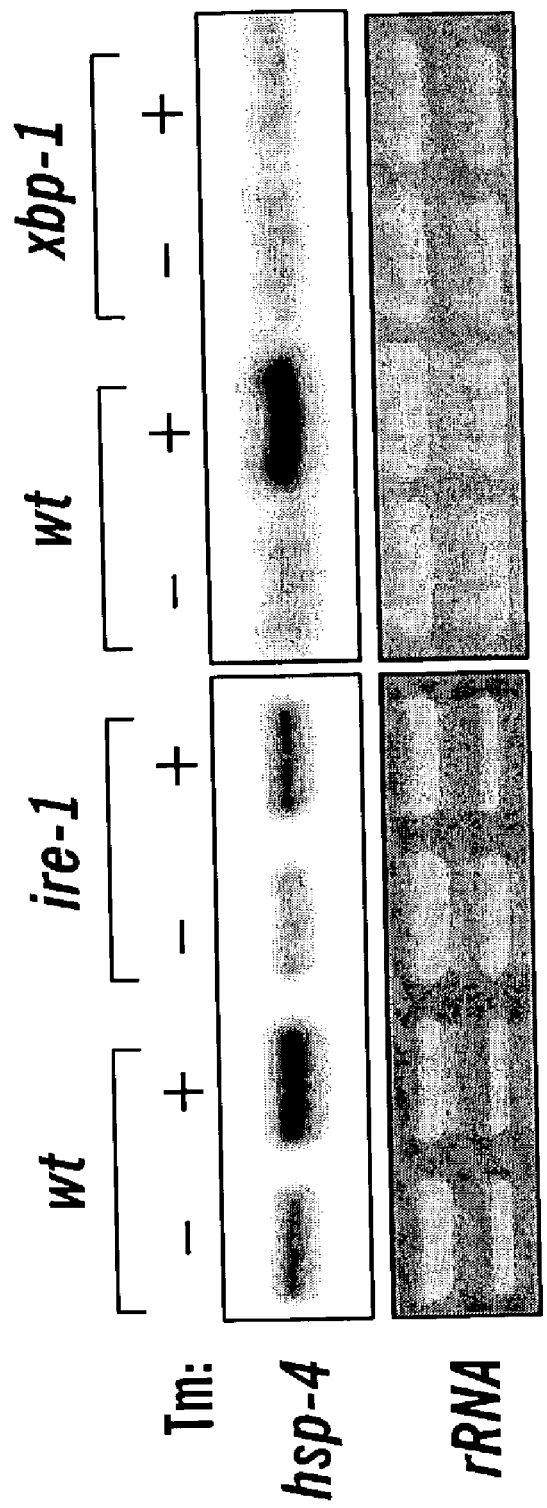

As in the regulation of HAC1 in yeast, mammalian IRE1 acts as a site-specific endonuclease to cleave the mRNA of a bZIP transcription-factor. Cleavage and removal of a small intron is followed by religation of the 5' and 3' fragments to produce a processed mRNA that is translated more efficiently and encodes a more stable protein. These findings provide new insight into the organization and evolution of the metazoan UPR. In yeast, virtually all genes activated in the UPR are IRE1- and HAC1-dependent (Travers et al., "Functional and Genomic Analyses Reveal an Essential Coordination Between the Unfolded Protein Response and ER-Associated Degradation," *Cell* 101:249-258 (2000); and Casagrande et al., "Degradation of Proteins From the ER of *S. Cerevisiae* Requires an Intact Unfolded Protein Response Pathway," *Mol. Cell* 5:729-735 (2000), which are hereby incorporated by reference in their entirety). Nematodes lacking ire-1 or xbp-1 function are also unable to induce hsp-4 (BiP) and other target genes of the UPR (FIG. 3J). By contrast, IRE1 mutant mammalian cells have no obvious defect in inducing UPR markers such as CHOP or XBP-1 itself (FIG. 4C). Mammalian evolution was apparently associated with specialization in IRE1 and XBP-1 function, diverting them from control of many UPR target genes towards certain specific cellular functions. The phenotype of the XBP-1–/– mouse may provide a clue to the nature of that specialization. RAG1-/-mice whose lymphoid system has been reconstituted with XBP-1–/– cells have a profound defect in immunoglobulin secretion that reflects impaired differentiation of B-cells to plasma cells (Reimold et al., "Plasma Cell Differentiation Requires the Transcription Factor XBP-1," *Nature* 412:300-307 (2001), which is hereby incorporated by reference in its entirety). The distinction between a plasma cell and B-cell is based on acquisition of the ability to secrete large amounts of immunoglobulin and its morphological corollary, an elaborate ER. The finding that IRE1 controls XBP-1 expression suggests, therefore, that increased load of client proteins in the ER activates XBP-1 and triggers development of an elaborate secretory apparatus, the hallmark of a plasma cell.

Recent reports lend further support to use of the method of the present invention to identify and develop therapeutic compounds that can be used to treat or prevent multiple myeloma and other diseases associated with plasma cell hyperactivity or misdirected activity (Claudio et al., "A Molecular Compendium of Genes Expressed In Multiple Myeloma," *Blood* 100(6):2175-2186 (2002); Gass et al., "Activation of An Unfolded Protein Response During Differentiation of Antibody-Secreting B Cells," *J. Biol. Chem.* 277(6):49047-49054 (2002); Calame et al., "Regulatory Mechanisms That Determine the Development and Function of Plasma Cells," *Annu. Rev. Immunol.* 21:205-230 (2003); and Iwakoshi et al., "Plasma Cell Differentiation and the Unfolded Protein Response Intersect At the Transcription Factor XBP-1," *Nature Immunology* 4(4):321-329 (2003), which are hereby incorporated by reference in their entirety).

Other recent reports suggest that viral infection activates signaling by IRE1 and XBP-1, and, therefore, such signaling may also play an important role in allowing viruses to assemble so-called replication factories in cells (see Felmlee et al., "Hepatitis C Virus Induces ER Stress; XBP-1 Converges Disease and Replication," In *Conformational Diseases of the Secretory Pathway* Taos, N. Mex., p. 113 (2003), which is hereby incorporated by reference in its entirety). If compounds can be found or designed that inhibit assembly of these virus replication factories, then methods can be developed to detect virus infection and prevent its spread. Thus, compounds identified as inhibiting IRE1-mediated processing of XBP-1 may have broad utility as anti-viral agents, including, without limitation, viruses infecting mammals.

Example 8

Detection of XBP-1 Activity In Living Human T Cells

Experiments have been conducted to develop assays for detecting IRE1-mediated XBP-1 mRNA processing in living mammalian cells. One such experiment involved the use of Gal4-Vp16 (SEQ ID NO:8), which is an artificial gene that encodes the DNA binding domain of yeast GAL4 fused to the transcription activation domain of the Herpes Simplex Virus VP16 gene. A schematic of how XBP-1 activity is detected is shown in FIGS. 9A-9E. The encoded fusion protein, GAL4-VP16, binds to special GAL4 UAS sites. Such sites are normally absent in mammalian genes, but can be introduced into a Luciferase reporter gene as shown in FIGS. 9D and 9E. This UAS-Luciferase reporter is therefore subordinate to activation by GAL4-VP16, which is normally absent in mammalian cells. As shown in FIG. 9A, the GAL4-VP16 coding region was fused into the XBP-1 gene in such a way as to make GAL4-VP16 continuous with the open reading frame generated after the IRE1-mediated excision of the small intron in XBP-1 (i.e., the event that normally activates XBP-1, as shown in FIG. 9B). The configuration of the fused gene after XBP-1 processing is shown schematically in FIG. 9C.

In unstressed cells, in which IRE1 is inactive, this XBP-1-GAL4-VP16 fusion gene makes no GAL4-VP-16 protein as the translation of XBP-1 mRNA terminates before the coding region of GAL4-VP16 and the UAS-Luciferase reporter gene is relatively silent (as shown schematically in FIG. 9D). Under conditions of ER stress, when IRE1 is active, the small intron in XBP-1 is removed, the reading frame is shifted and the GAL4-VP16 coding region is translated in continuity with XBP-1 (see FIG. 9B). At that moment, the UAS-Luciferase reporter gene is engaged by the fusion protein and Luciferase protein is made (as shown in FIG. 9E). Cells expressing UAS-Luciferase and the XBP-1-GAL4-VP16 gene serve as sensitive reporters for activity of the IRE1 and XBP-1 signaling pathway and are therefore suitable for high-throughput screens of activators and inhibitors of the pathway.

Figure 10:
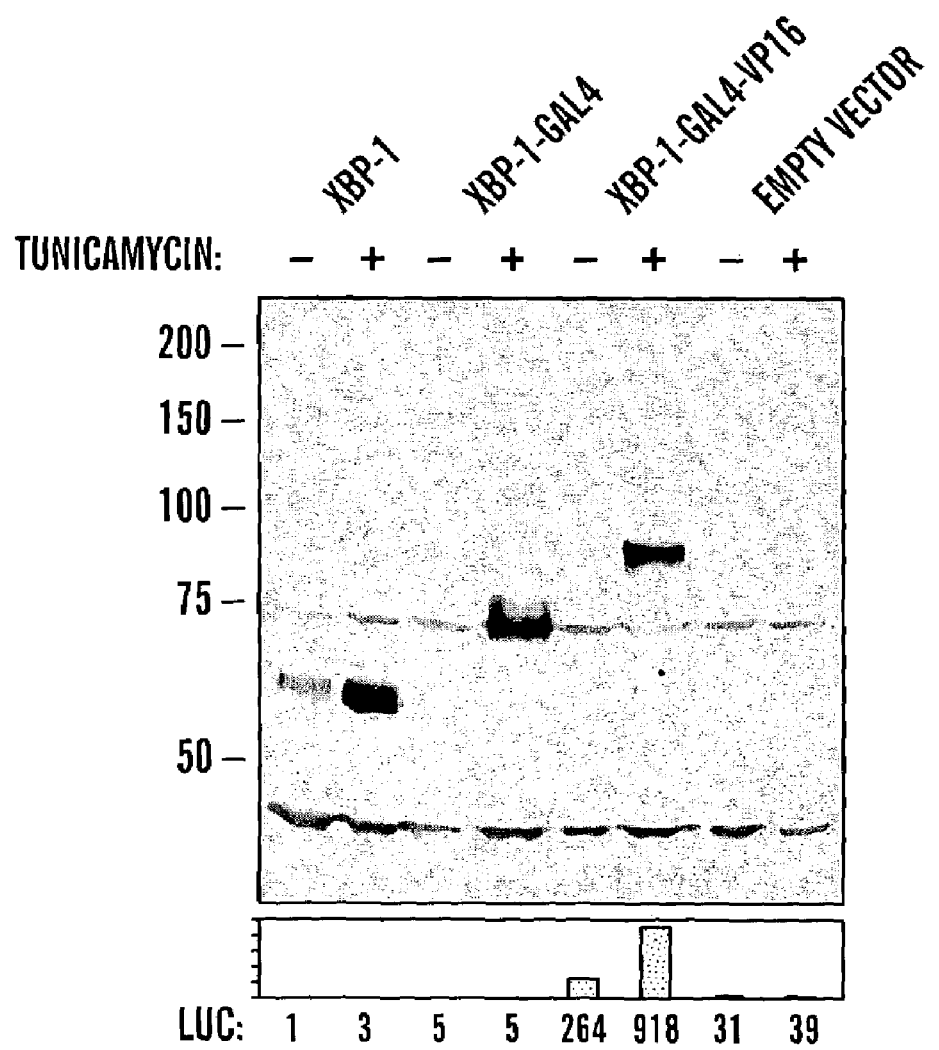
FIG. 10 is a diagram showing Luciferase activity in the absence and presence of an ER stress inducing agent in the presence of various XBP-1 activator plasmids. The top panel is an immunoblot of proteins in lysates of human 293T cells transfected with plasmids encoding the indicated genes. The cells remained untreated or were treated with an ER stress-inducing agent tunicamycin ($0.4_x$ mg/mL for 16 hours). The bottom panel shows the level of Luciferase activity in 293T cells co-transfected with a UAS-Luciferase reporter plasmid and the indicated XBP-1 activator plasmids following tunicamycin treatment as above.

FIG. 10 shows the immunoblot and Luciferase activity readings from the experiment described above in this Example 8. The top panel of FIG. 10 shows an immunoblot of proteins in lysates of human 293T cells transfected with plasmids encoding the indicated genes. The cells remained untreated or were treated with the ER stress-inducing agent tunicamycin (0.4 mg/mL for 16 hours). The bottom panel of FIG. 10 shows the level of Luciferase activity in 293T cells co-transfected with a UAS-Luciferase reporter plasmid and the indicated XBP-1 activator plasmids following tunicamycin treatment as above.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of screening a compound for potential effectiveness in treating a mammalian disease mediated by plasma cells, said method comprising:

providing a test compound;

providing an assay system suitable for evaluating the test compound's ability to inhibit processing of unspliced X-Box binding protein 1 (XBP-1) mRNA to spliced XBP-1 mRNA, said assay system comprising:
  unspliced XBP-1 mRNA;
  IRE1 protein; and
  a system suitable to splice unspliced XBP-1 mRNA;

contacting the test compound with the assay system and providing a stimulus effective to activate processing of unspliced XBP-1 mRNA to spliced XBP-1 mRNA with IRE1 present;

evaluating, with the assay system, the test compound's ability to inhibit IRE1-mediated processing of unspliced XBP-1 mRNA to spliced XBP-1 mRNA by IRE1 by detecting whether unspliced XBP-1 mRNA and spliced XBP-1 mRNA are present in the assay system with and without the test compound; and identifying test compounds which reduce spliced XBP-1 mRNA and increase unspliced XBP-1 mRNA as having potential effectiveness in treating a mammalian disease mediated by plasma cells.

2. The method according to claim 1, wherein said detecting comprises use of a polymerase chain reaction process to analyze whether unspliced XBP-1 mRNA and spliced XBP-1 mRNA are present.

3. The method according to claim 1, wherein said mammalian disease is caused by pathogenic immunoglobulins secreted from said plasma cells.

4. The method according to claim 3, wherein said mammalian disease is selected from the group consisting of Myasthenia Gravis, Pemphigus Vulgaris, Systemic Lupus Lrythromatosus, Guillain Barré syndrome, proliferative glomerulonephritis, hemophilia with inhibitory antibodies to factor 8, hemophilia with inhibitory antibodies to factor 9, autoimmune thrombocytopenia, autoimmune hemolytic anemia, and paraneoplastic syndrome.

5. The method according to claim 1, wherein said mammalian disease is a cancer caused by the abnormal proliferation of plasma cells.

6. The method according to claim 5, wherein said cancer is Multiple Myeloma or plasma cell dyscrasia.

7. A method of screening a compound for potential effectiveness in treating a mammalian disease caused by virus infection of mammalian cells, said method comprising:

providing a test compound;

providing an assay system suitable for evaluating the test compound's ability to inhibit processing of unspliced XBP-1 mRNA to spliced XBP-1 mRNA, said assay system comprising:

unspliced XBP-1 mRNA;

IRE1 protein; and a system suitable to splice unspliced XBP-1 mRNA;

contacting the test compound with the assay system and providing a stimulus effective to activate processing of unspliced XBP-1 mRNA to spliced XBP-1 mRNA with IRE1 present;

evaluating, with the assay system, the test compound's ability to inhibit IRE1-mediated processing of unspliced XBP-1 mRNA to spliced XBP-1 mRNA by IRE1 by detecting whether unspliced XBP-1 mRNA and spliced XBP-1 mRNA are present in the assay system with and without the test compound; and identifying test compounds which reduce spliced XBP-1 mRNA and increase unspliced XBP-1 mRNA as having potential effectiveness in treating a mammalian disease caused by virus infection of mammalian cells.

* * * * *